United States Patent
Liang et al.

(10) Patent No.: US 11,154,841 B2
(45) Date of Patent: Oct. 26, 2021

(54) MIXED OXIDES CATALYSTS FOR OXIDATIVE COUPLING OF METHANE

(71) Applicants: Wugeng Liang, Sugar Land, TX (US); Luanyi Li, Sugar Land, TX (US); Vidya Sagar Reddy Sarsani, Sugar Land, TX (US); Hector Perez, Sugar Land, TX (US); David West, Sugar Land, TX (US); Sabic Global Technologies, B.V., Bergen Op Zoom (NL)

(72) Inventors: Wugeng Liang, Sugar Land, TX (US); Luanyi Li, Sugar Land, TX (US); Vidya Sagar Reddy Sarsani, Sugar Land, TX (US); Hector Perez, Sugar Land, TX (US); David West, Sugar Land, TX (US)

(73) Assignee: Sabic Global Technologies, B.V., Bergen Op Zoom (NL)

(*) Notice: Subject to any disclaimer, the term of this patent is extended or adjusted under 35 U.S.C. 154(b) by 0 days.

(21) Appl. No.: 17/252,828

(22) PCT Filed: Aug. 7, 2019

(86) PCT No.: PCT/US2019/045480
§ 371 (c)(1),
(2) Date: Dec. 16, 2020

(87) PCT Pub. No.: WO2020/033529
PCT Pub. Date: Feb. 13, 2020

(65) Prior Publication Data
US 2021/0154644 A1     May 27, 2021

Related U.S. Application Data

(60) Provisional application No. 62/716,644, filed on Aug. 9, 2018.

(51) Int. Cl.
*B01J 23/10* (2006.01)
*B01J 23/04* (2006.01)
(Continued)

(52) U.S. Cl.
CPC ............... *B01J 23/10* (2013.01); *B01J 23/04* (2013.01); *B01J 35/1009* (2013.01);
(Continued)

(58) Field of Classification Search
USPC .......................................................... 502/303
See application file for complete search history.

(56) References Cited

U.S. PATENT DOCUMENTS

| 2008/0175779 A1* | 7/2008 | Cao ........................... C30B 7/00 423/263 |
| 2013/0165728 A1 | 6/2013 | Zurcher et al. |

(Continued)

FOREIGN PATENT DOCUMENTS

| EA | 029490 B1 | 4/2018 |
| KR | 20120109998 A | 10/2012 |

(Continued)

OTHER PUBLICATIONS

Filing Receipt and Specification of U.S. Appl. No. 62/716,644, filed Aug. 9, 2018, 55 pages.

(Continued)

*Primary Examiner* — Douglas B Call
(74) *Attorney, Agent, or Firm* — Rodney B. Carroll; Conley Rose, P.C.

(57) ABSTRACT

An OCM nanoplate catalyst comprising ≥25 wt. % nanoplates; wherein a nanoplate is a three-dimensional object defined in accordance with ISO/TS 80004-2:2015; wherein a nanoplate is characterized by a first external dimension (thickness (t)≤100 nm), a second external dimension (length (l)>t), and a third external dimension (width (w)>t); wherein (Continued)

l and w can be the same or different; and wherein l≥5 t, w≥5 t, or l≥5 t and w≥5 t; and wherein the OCM nanoplate catalyst has general formula $A_aZ_bE_cD_dO_x$; wherein A=alkaline earth metal; Z=first rare earth element; E=second rare earth element; D=redox agent/third rare earth element; wherein the first, second, and third rare earth element are not the same; wherein a=1.0; wherein b=1.0 to 3.0; wherein c=0 to 1.5; wherein d=0 to 1.5; wherein (b>(c+d)); and wherein x balances the oxidation states.

22 Claims, 8 Drawing Sheets

(51) Int. Cl.
  B01J 35/10    (2006.01)
  B01J 37/08    (2006.01)
  C01B 3/38     (2006.01)
  C07C 2/84     (2006.01)
  C07C 11/04    (2006.01)
  B82Y 30/00    (2011.01)
  B82Y 40/00    (2011.01)

(52) U.S. Cl.
  CPC ......... B01J 35/1038 (2013.01); B01J 37/08 (2013.01); C01B 3/38 (2013.01); C07C 2/84 (2013.01); C07C 11/04 (2013.01); B82Y 30/00 (2013.01); B82Y 40/00 (2013.01); C01B 2203/1241 (2013.01)

(56) References Cited

U.S. PATENT DOCUMENTS

2016/0074844 A1* 3/2016 Freer .................. B01J 37/0009
                                                    585/658
2016/0107143 A1    4/2016 Schammel et al.

FOREIGN PATENT DOCUMENTS

RU    2647844 C1      3/2018
WO    2018085820 A1   5/2018
WO    2018085826 A1   5/2018
WO    2020033529 A1   2/2020

OTHER PUBLICATIONS

Foreign Communication from a related application—International Search Report and Written Opinion of the International Searching Authority of Application No. PCT/US2019/045480 dated Nov. 26, 2019, 6 pages.

Balakotaiah, Vemuri, et al., "Runaway Limits for Homogeneous and Catalytic Reactors," Chemical Engineering Science, 1995, pp. 1149-1171, vol. 50, No. 7, Elsevier Science Ltd.

Hoebink, J.H.B.J., et al., "Fixed Bed Reactor Design for Gas Phase Chain Reactions Catalysed by Solids: The Oxidative Coupling of Methane," Chemical Engineering Science, 1994, pp. 5453-5463, vol. 49, No. 24B, Elsevier Science Ltd.

Lomonosov, V.I., et al., "Oxidative Coupling of Methane: Mechanism and Kinetics," Kinetics and Catalysis, 2016, pp. 647-676, vol. 57, No. 5, Pleiades Publishing Ltd.

Noon, Daniel, et al., "Oxidative Coupling of Methane by Nanofiber Catalysts," ChemCatChem Communications, 2013, pp. 146-149, vol. 5, ChemPubSoc Europe.

Tarasov, Andrei L., et al., "Autothermal Methane Oxidative Coupling Process over La2O3/MgO Catalysts," Chem. Eng. Technol., 2015, pp. 2243-2252, vol. 38, No. 12, Wiley-VCH Verlag GmbH & Co. KGaA.

Zavyalova, Ulyana, et al., "Statistical Analysis of Past Catalytic Data on Oxidative Methane Coupling for New Insights into the Composition of High-Performance Catalysts," ChemCatChem, 2011, pp. 1935-1947, vol. 3, Wiley-VCH Verlag GmbH & Co. KGaA.

Kolesnikov, I. M., et al., "Solid catalysts, their structure, composition and catalytic activity: Monograph 1," GUP Publisher "Neft and gaz" of Gubkin Russian State University of Oil and Gas, 2000, 372 p., Moscow.

Kolesnikov, I. M., "Catalysis in the gas-oil industry," Moscow, 2012, p. 297.

Official Action dated May 20, 2021 and Search Report dated May 19, 2021 of Russian Patent Application No. 2021102473, 21 pages (including translation).

* cited by examiner

MIXED OXIDES CATALYSTS FOR OXIDATIVE COUPLING OF METHANE

CROSS REFERENCE TO RELATED APPLICATIONS

This application is a filing under 35 U.S.C. 371 of International Application No. PCT/US2019/045480 filed Aug. 7, 2019, entitled "Mixed Oxides Catalysts for Oxidative Coupling of Methane" which claims priority to U.S. Provisional Application No. 62/716,644 filed Aug. 9, 2018, which applications are incorporated by reference herein in their entirety.

TECHNICAL FIELD

The present disclosure relates to catalyst compositions for oxidative coupling of methane (OCM), more specifically nanoplate catalyst compositions based on oxides of alkaline earth metals, and rare earth elements for OCM, and methods of making and using same.

BACKGROUND

Hydrocarbons, and specifically olefins such as ethylene, are typically building blocks used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes.

Oxidative coupling of the methane (OCM) has been the target of intense scientific and commercial interest for more than thirty years due to the tremendous potential of such technology to reduce costs, energy, and environmental emissions in the production of ethylene ($C_2H_4$). As an overall reaction, in the OCM, methane ($CH_4$) and oxygen ($O_2$) react exothermically over a catalyst to form $C_2H_4$, water ($H_2O$) and heat.

Ethylene can be produced by OCM as represented by Equations (I) and (II):

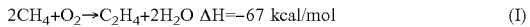

$$2CH_4 + O_2 \rightarrow C_2H_4 + 2H_2O \quad \Delta H = -67 \text{ kcal/mol} \quad (I)$$

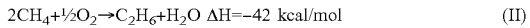

$$2CH_4 + \tfrac{1}{2}O_2 \rightarrow C_2H_6 + H_2O \quad \Delta H = -42 \text{ kcal/mol} \quad (II)$$

Oxidative conversion of methane to ethylene is exothermic. Excess heat produced from these reactions (Equations (I) and (II)) can push conversion of methane to carbon monoxide and carbon dioxide rather than the desired $C_2$ hydrocarbon product (e.g., ethylene):

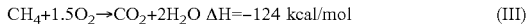

$$CH_4 + 1.5O_2 \rightarrow CO_2 + 2H_2O \quad \Delta H = -124 \text{ kcal/mol} \quad (III)$$

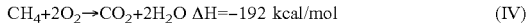

$$CH_4 + 2O_2 \rightarrow CO_2 + 2H_2O \quad \Delta H = -192 \text{ kcal/mol} \quad (IV)$$

The excess heat from the reactions in Equations (III) and (IV) further exasperate this situation, thereby substantially reducing the selectivity of ethylene production when compared with carbon monoxide and carbon dioxide production.

Additionally, while the overall OCM is exothermic, catalysts are used to overcome the endothermic nature of the C—H bond breakage. The endothermic nature of the bond breakage is due to the chemical stability of methane, which is a chemically stable molecule due to the presence of its four strong tetrahedral C—H bonds (435 kJ/mol). When catalysts are used in the OCM, the exothermic reaction can lead to a large increase in catalyst bed temperature and uncontrolled heat excursions that can lead to catalyst deactivation and a further decrease in ethylene selectivity. Furthermore, the produced ethylene is highly reactive and can form unwanted and thermodynamically favored deep oxidation products.

Generally, in the OCM, $CH_4$ is first oxidatively converted into ethane ($C_2H_6$), and then into $C_2H_4$. $CH_4$ is activated heterogeneously on a catalyst surface, forming methyl radicals (e.g., $CH_{3*}$), which then couple in a gas phase to form $C_2H_6$. $C_2H_6$ subsequently undergoes dehydrogenation to form $C_2H_4$. An overall yield of desired $C_2$ hydrocarbons is reduced by non-selective reactions of methyl radicals with oxygen on the catalyst surface and/or in the gas phase, which produce (undesirable) carbon monoxide and carbon dioxide. Some of the best reported OCM outcomes encompass a ~20% conversion of methane and ~80% selectivity to desired $C_2$ hydrocarbons.

There are many catalyst systems developed for OCM processes, but such catalyst systems have many shortcomings. For example, conventional catalysts systems for OCM display catalyst performance problems, stemming from a need for high reaction temperatures to achieve desired conversions and selectivities. Thus, there is an ongoing need for the development of catalyst compositions for OCM processes.

BRIEF DESCRIPTION OF THE DRAWINGS

For a detailed description of the preferred aspects of the disclosed methods, reference will now be made to the accompanying drawing in which.

DETAILED DESCRIPTION

Figure 1:
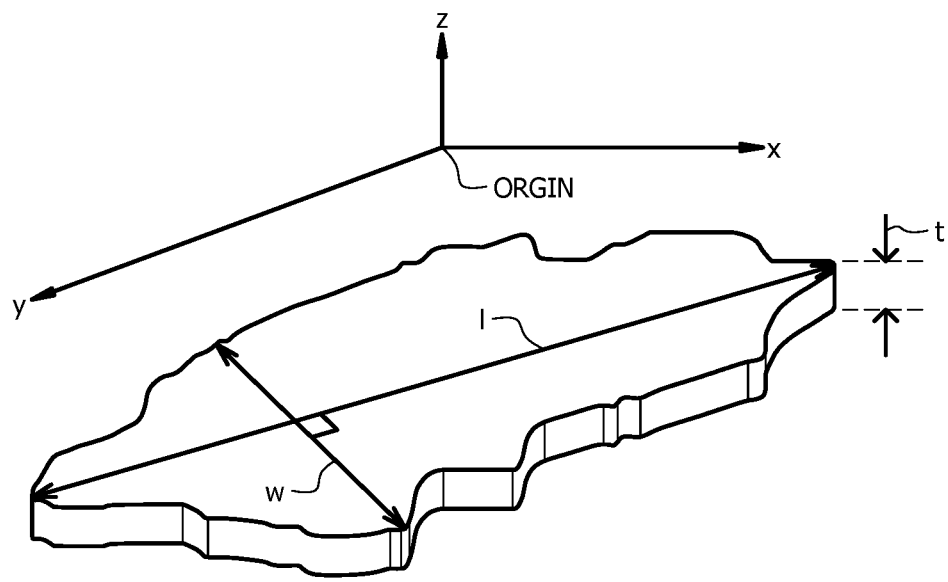
FIG. 1 displays a schematic diagram of a nanoplate.

Disclosed herein are oxidative coupling of methane (OCM) nanoplate catalyst compositions and methods of making and using same. In an aspect, an OCM nanoplate catalyst composition can comprise equal to or greater than about 25 wt. % nanoplates, based on the total weight of the OCM nanoplate catalyst composition; wherein a nanoplate is a three-dimensional object defined in accordance with ISO/TS 80004-2:2015; wherein the OCM nanoplate catalyst composition is characterized by the general formula $A_a$ $Z_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 1.0 to about 3.0; wherein c is from about 0 to about 1.5; wherein d is from about 0 to about 1.5; wherein b is greater than the sum of c and d (b>(c+d)); and wherein x balances the oxidation states.

A method of making an OCM nanoplate catalyst composition can generally comprise the steps of (a) forming an OCM nanoplate catalyst precursor mixture; wherein the OCM nanoplate catalyst precursor mixture comprises a nitrate comprising an alkaline earth metal cation, a nitrate comprising a first rare earth element cation, a nitrate comprising a second rare earth element cation, and a nitrate comprising a redox agent cation or a third rare earth element cation; wherein the first rare earth element cation, the second rare earth element cation, and the third rare earth element cation, when present, are not the same; wherein the OCM nanoplate catalyst precursor mixture is characterized by a molar ratio of first rare earth element to alkaline earth metal of b:1, wherein b is from about 1.0 to about 3.0; wherein the OCM nanoplate catalyst precursor mixture is characterized by a molar ratio of second rare earth element to alkaline earth metal of c:1, wherein c is from about 0 to about 1.5; and wherein the OCM nanoplate catalyst precursor mixture is characterized by a molar ratio of redox agent or third rare earth element to alkaline earth metal of d:1, wherein d is from about 0 to about 1.5; and (b) calcining at least a portion of the OCM nanoplate catalyst precursor mixture at a temperature of equal to or greater than about 750° C. to form the OCM nanoplate catalyst composition.

In an aspect, the OCM nanoplate catalyst composition disclosed herein can be employed in an OCM process for the production of olefins, such as ethylene.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through the carbon of the carbonyl group.

In an aspect, an oxidative coupling of methane (OCM) nanoplate catalyst composition can comprise equal to or greater than about 25 wt. %, alternatively equal to or greater than about 30 wt. %, alternatively equal to or greater than about 35 wt. %, alternatively equal to or greater than about 40 wt. %, alternatively equal to or greater than about 45 wt. %, alternatively equal to or greater than about 50 wt. %, alternatively equal to or greater than about 55 wt. %, alternatively equal to or greater than about 60 wt. %, alternatively equal to or greater than about 65 wt. %, alternatively equal to or greater than about 70 wt. %, alternatively equal to or greater than about 75 wt. %, alternatively equal to or greater than about 80 wt. %, alternatively equal to or greater than about 85 wt. %, alternatively equal to or greater than about 90 wt. %, alternatively equal to or greater than about 95 wt. %, or alternatively equal to or greater than about 99 wt. % nanoplates, based on the total weight of the OCM nanoplate catalyst composition; wherein a nanoplate is a three-dimensional object defined in accordance with ISO/TS 80004-2:2015. In an aspect, the OCM nanoplate catalyst composition consists of or consists essentially of nanoplates, wherein a nanoplate is a three-dimensional object defined in accordance with ISO/TS 80004-2:2015.

In an aspect, a nanoplate can be characterized by a first external dimension, a second external dimension, and a third external dimension; wherein the first external dimension is the thickness (t) of the nanoplate, and wherein t is equal to or less than about 100 nm, alternatively equal to or less than about 90 nm, alternatively equal to or less than about 80 nm, alternatively equal to or less than about 75 nm, alternatively equal to or less than about 50 nm, alternatively equal to or less than about 25 nm, or alternatively equal to or less than about 10 nm; wherein the second external dimension is the length (l) of the nanoplate, and wherein l is greater than t (l>t); wherein the third external dimension is the width (w) of the nanoplate, and wherein w is greater than t (w>t). In some aspects, l and w can be the same (l=w). In other aspects, l and w can be different.

Generally, a nanoplate can be placed in a three-dimensional Cartesian coordinate system (i.e., a Cartesian coordinate system for a three-dimensional space) having axes x, y, and z; for example as shown in FIG. 1. A three-dimensional Cartesian coordinate system has 3 axes (x, y, and z) that go through a common point (origin), wherein the axes are perpendicular to each other and define coordinate planes: x and y are perpendicular to each other and define the coordinate plane xy (xy-plane); x and z are perpendicular to each other and define the coordinate plane xz (xz-plane); and y and z are perpendicular to each other and define the coordinate plane yz (yz-plane).

For purposes of the disclosure herein, a nanoplate can be placed in a three-dimensional Cartesian coordinate system such that t is defined along the z axis, for example as shown in FIG. 1. t is the thickness of the nanoplate along the direction of the z axis, wherein the thickness can be non-uniform across the nanoplate, and wherein t is equal to or less than about 100 nm anywhere in the nanoplate. Further, for purposes of the disclosure herein, l and w are defined in any xy-plane plane (which is perpendicular to z) that can provide for a nanoplate cross section. Furthermore, for purposes of the disclosure herein, l is the largest dimension of any two-dimensional cross section in any xy-plane through a nanoplate; and w is the largest dimension perpendicular to l in the x-y plane where l is defined; for example as shown in FIG. 1.

In an aspect, the nanoplates suitable for use in the present disclosure are characterized by (i) l being equal to or greater than about 5 t (l≥5 t), alternatively l≥7.5 t, or alternatively l≥10 t; (ii) w being equal to or greater than about 5 t (w≥5 t), alternatively w≥7.5 t, or alternatively w≥10 t; or (iii) l≥5 t, alternatively l≥7.5 t, or alternatively l≥10 t and w≥5 t, alternatively w≥7.5 t, or alternatively w≥10 t.

As will be appreciated by one of skill in the art, and with the help of this disclosure, and without wishing to be limited by theory, in the case of a catalyst having a nanoplate-type structure (e.g., nanoplate-type structural features), for example as shown in FIG. 1, the active sites in the catalyst are more likely (e.g., have a higher chance) to be present on an external surface (e.g., exposed external surface) of the catalyst, for example, on each of the two external catalyst surfaces located in an xy-plane as shown in FIG. 1; given that the majority of the external surface area of the catalyst as depicted in FIG. 1 is located in an xy-plane, and given that the catalyst as depicted in FIG. 1 has a fairly large external surface area with respect to its volume. Further, as will be appreciated by one of skill in the art, and with the help of this disclosure, and without wishing to be limited by theory, when more active sites are located at an external surface (e.g., are exposed), reactants have more chances to access such active sites (owing to a geometry that does not hinder diffusion), thereby resulting in higher catalyst activity.

Furthermore, as will be appreciated by one of skill in the art, and with the help of this disclosure, and without wishing to be limited by theory, in the case of a catalyst having a nanoplate-type structure (e.g., nanoplate-type structural features), for example as shown in FIG. 1, the nanoplate-type structure can provide for an enhanced desorption of methyl radicals and $C_{2+}$ products formed on the external catalyst surface (owing to a geometry that does not hinder diffusion), thereby decreasing deep oxidation reactions and increasing selectivity.

In an aspect, the OCM nanoplate catalyst composition as disclosed herein can be characterized by an open pore structure. Generally, an open pore structure refers to the pores of a porous material being fluidly connected to each other and to the exterior of the material, i.e., a gas or liquid can travel from one pore to another (e.g., a gas or liquid can diffuse between pores in a material having an open pore structure) and from the exterior of the material into the pores and vice versa. By contrast, a closed pore structure refers to the pores of a porous material being partially or completely surrounded by solid material, wherein the pores are not fully fluidly connected to each other, i.e., a gas or liquid cannot travel or travel with high resistance from one pore to another (e.g., a gas or liquid cannot diffuse between pores in a material having a closed pore structure). As will be appreciated by one of skill in the art, and with the help of this disclosure, some pores located proximal to an exterior surface of a material having a closed pore structure can be fluidly connected to the exterior of the material.

The OCM nanoplate catalyst composition can have any suitable desired total pore volume specifications, for example as required by a specific application. For example, the OCM nanoplate catalyst composition as disclosed herein can be characterized by a total pore volume of equal to or greater than about 0.02 cc/g, alternatively equal to or greater than about 0.03 cc/g, alternatively equal to or greater than about 0.05 cc/g, or alternatively equal to or greater than about 0.1 cc/g, as determined according to the Brunauer, Emmett and Teller (BET) method; although any other suitable OCM nanoplate catalyst composition total pore volumes can be employed. Generally, the total pore volume of a porous material refers to the total void volume of the material divided by the mass of the material.

In an aspect, the OCM nanoplate catalyst composition as disclosed herein can be characterized by a total pore volume that is increased by equal to or greater than about 10%, alternatively equal to or greater than about 20%, alternatively equal to or greater than about 30% when compared to a total pore volume of an otherwise similar OCM catalyst composition comprising less than about 25 wt. % nanoplates, based on the total weight of the composition.

In an aspect, the OCM nanoplate catalyst composition as disclosed herein can be characterized by an average pore diameter that is increased by equal to or greater than about 5%, alternatively equal to or greater than about 10%, alternatively equal to or greater than about 15% when compared to an average pore diameter of an otherwise similar OCM catalyst composition comprising less than about 25 wt. % nanoplates, based on the total weight of the composition.

The OCM nanoplate catalyst composition can have any suitable desired specific surface area specifications, for example as required by a specific application. For example, the OCM nanoplate catalyst composition can be characterized by a specific surface area of equal to or greater than about 1.5 $m^2/g$, alternatively equal to or greater than about 2.5 $m^2/g$, or alternatively equal to or greater than about 5 $m^2/g$, as determined by measuring nitrogen adsorption according to the BET method; although any other suitable OCM nanoplate catalyst composition specific surface areas can be employed. Generally, the specific surface area of a solid material refers to the total surface area of the material divided by the mass of the material. Specific surface area can be determined by measuring the amount of physically adsorbed gas (e.g., nitrogen) according to the BET method.

As will be appreciated by one of skill in the art, and with the help of this disclosure, as the porosity of a material increases, the specific surface area of the material increases as well. Generally, the porosity of a material refers to the percentage volume occupied by pores or void space within a total volume of the material. In an aspect, the OCM nanoplate catalyst composition as disclosed herein is characterized by a porosity that is higher than a porosity of an otherwise similar OCM catalyst composition comprising less than about 25 wt. % nanoplates, based on the total weight of the composition.

In an aspect, the OCM nanoplate catalyst composition as disclosed herein can be characterized by a specific surface area that is increased by equal to or greater than about 20%, alternatively equal to or greater than about 35%, alternatively equal to or greater than about 50% when compared to a specific surface area of an otherwise similar OCM catalyst composition comprising less than about 25 wt. % nanoplates, based on the total weight of the composition.

Without wishing to be limited by theory, an increased catalyst specific surface area and pore volume can reduce diffusion resistance (e.g., diffusion resistance of reactant mixture components, reactive species, product mixture components, etc.; internal mass transfer resistance). Further, and without wishing to be limited by theory, a porous catalyst structure can provide for an increased number of catalytically active sites being accessible to reactants, thereby resulting in higher catalyst activity.

Without wishing to be limited by theory, the OCM reaction can propagate by following a mechanism according to reactions (1)-(5):

$$[O]_s + CH_4 \rightarrow [OH]_s + CH_3 \quad (1)$$

$$2CH_3 \rightarrow C_2H_6 \quad (2)$$

$$CH_3 + O_2 \leftrightarrow CH_3O_2 \quad (3)$$

$$CH_3 + [O]_s \leftrightarrow [CH_3O]_s \quad (4)$$

$$2[OH]_s + \tfrac{1}{2}O_2 \rightarrow 2[O]_s + H_2O \quad (5)$$

wherein "s" denotes a species adsorbed onto the catalyst surface. As will be appreciated by one of skill in the art, and with the help of this disclosure, two or more of reactions (1)-(5) can occur concurrently (as opposed to sequentially). According to reaction (1), the activation of methane occurs with the participation of active adsorbed oxygen sites $[O]_s$, leading to the formation of methyl radicals and adsorbed hydroxyl group $[OH]_s$. According to reaction (2), the coupling of methyl radicals to form the coupling product ethane ($C_2H_6$) occurs in gas phase; wherein reaction (2) has a low activation energy, and therefore, does not limit the overall reaction rate. According to reaction (3), methyl radicals can react with gas phase oxygen to form an oxygenate product $CH_3O_2$. According to reaction (4), methyl radicals can also re-adsorb on to the catalyst surface and react with surface oxygen (e.g., active adsorbed oxygen sites $[O]_s$) to form an oxygenate species $[CH_3O]_s$. The oxygenates formed according to reactions (3) and (4) can further form CO and $CO_2$, and as such the reaction steps according to reactions (3) and (4) are the main reactions controlling the selectivity of various OCM catalysts. The mechanism of OCM reaction is described in more detail in Lomonosov, V. I. and Sinev, M. Y., Kinetics and Catalysis, 2016, vol. 57, pp. 647-676; which is incorporated by reference herein in its entirety.

As previously discussed herein, and without wishing to be limited by theory, in the case of a catalyst having a nanoplate-type structure (e.g., nanoplate-type structural features), for example as shown in FIG. 1, which structure results in more active sites accessible on the external catalyst surface, there will be more $[O]_s$ accessible to the reactant $CH_4$, such that the reaction rate of reaction (1) will be increased, thereby resulting in an increased catalyst activity.

Further, and without wishing to be limited by theory, the methyl radical can leave the catalyst surface easier once it is formed (e.g., owing to the nanoplate-type structure and increased porosity), then the methyl radical will have less opportunity to form oxygenate species onto the catalyst surface (according to reaction (4)), which oxygenate species can be further oxidized to CO and $CO_2$. Furthermore, and without wishing to be limited by theory, a reduction in oxygenate species formation (e.g., owing to an increased specific surface area due to increased porosity) can increase the selectivity of the OCM reaction to desired $C_{2+}$ hydrocarbon products.

In an aspect, the OCM nanoplate catalyst composition as disclosed herein can be in the form of powders, particles, pellets, monoliths, foams, honeycombs, and the like, or combinations thereof. Nonlimiting examples of OCM nanoplate catalyst composition particle shapes include cylindrical, discoidal, spherical, tabular, ellipsoidal, equant, irregular, cubic, acicular, and the like, or combinations thereof.

The OCM nanoplate catalyst composition can have any suitable desired particle specifications, for example as required by a specific application. For example, the OCM nanoplate catalyst composition can be characterized by a size suitable for use in a particular reactor (e.g., OCM reactor). As will be appreciated by one of skill in the art, and with the help of this disclosure, the catalyst size can be determined for a particular application to achieve the best performance for the OCM reaction (e.g., desired conversion, desired selectivity, etc.).

In an aspect, an OCM nanoplate catalyst composition as disclosed herein can be characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 1.0 to about 3.0, alternatively from about 1.25 to about 2.75, or alternatively from about 1.5 to about 2.5; wherein c is from about 0 to about 1.5, alternatively from about 0.1 to about 1.25, or alternatively from about 0.5 to about 1.0; wherein d is from about 0 to about 1.5, alternatively from about 0.1 to about 1.25, or alternatively from about 0.5 to about 1.0; wherein b is greater than the sum of c and d (b>(c+d)); and wherein x balances the oxidation states. As will be appreciated by one of the skill in the art, and with the help of this disclosure, each of the A, Z, E and D can have multiple oxidation states within the OCM nanoplate catalyst composition, and as such x can have any suitable value that allows for the oxygen anions to balance all the cations. Without wishing to be limited by theory, the different metals (A, Z, E, and D) present in the OCM nanoplate catalyst composition as disclosed herein display synergetic effects in terms of conversion and selectivity. Further, and without wishing to be limited by theory, different ion radii and valences of the multiple metals (A, Z, E, and D) present in the OCM nanoplate catalyst composition as disclosed herein can generate formation of uncompensated oxygen vacancies, which can lead to further improvement of catalyst performance, for example in terms of conversion, selectivity, stability, etc.

The OCM nanoplate catalyst composition as disclosed herein can comprise an alkaline earth metal (A). The alkaline earth metal (A) can be selected from the group consisting of magnesium (Mg), calcium (Ca), strontium (Sr), barium (Ba), and combinations thereof. In an aspect, the alkaline earth metal (A) is strontium (Sr).

The OCM nanoplate catalyst composition as disclosed herein can comprise a first rare earth element (Z). The first rare earth element (Z) can be selected from the group consisting of lanthanum (La), neodymium (Nd), and combinations thereof. In an aspect, the first rare earth element (Z) is lanthanum (La).

The OCM nanoplate catalyst composition as disclosed herein can comprise a second rare earth element (E) and/or a third rare earth element (D), wherein E and D are different. The second rare earth element (E) and the third rare earth element (D) can each independently be selected from the group consisting of scandium (Sc), cerium (Ce), praseodymium (Pr), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

As will be appreciated by one of skill in the art, and with the help of this disclosure, in some aspects, the second rare earth element (E) can comprise a single rare earth element, such as ytterbium (Yb). Further, and as will be appreciated by one of skill in the art, and with the help of this disclosure, in some aspects, the second rare earth element (E) can comprise two or more rare earth elements, such as ytterbium (Yb), and thulium (Tm), for example.

Further, as will be appreciated by one of skill in the art, and with the help of this disclosure, in some aspects, the third rare earth element (D) can comprise a single rare earth element, such as ytterbium (Yb). Further, and as will be appreciated by one of skill in the art, and with the help of this disclosure, in some aspects, the third rare earth element (D) can comprise two or more rare earth elements, such as ytterbium (Yb), and lutetium (Lu), for example.

The OCM nanoplate catalyst composition as disclosed herein can comprise a redox agent (D). As will be appreciated by one of skill in the art, and with the help of this disclosure, D can be either a redox agent or a third rare earth element. The redox agent (D) can be selected from the group consisting of manganese (Mn), tungsten (W), bismuth (Bi), antimony (Sb), tin (Sn), cerium (Ce), praseodymium (Pr), and combinations thereof. A redox agent generally refers to a chemical species that possesses the ability to undergo both an oxidation reaction and a reduction reaction, and such ability usually resides in the chemical species having more than one stable oxidation state other than the oxidation state of zero (0). As will be appreciated by one of skill in the art, and with the help of this disclosure, some rare earth elements, such as Ce and Pr, can also be considered redox agents. Further, as will be appreciated by one of skill in the art, and with the help of this disclosure, when D is Ce and/or Pr, D can be considered either a redox agent or a third rare earth element.

In some aspects, the redox agent (D) is manganese (Mn). In other aspects, the redox agent (D) is tungsten (W).

As will be appreciated by one of skill in the art, and with the help of this disclosure, in some aspects, the redox agent (D) can comprise a single element, such as manganese (Mn). Further, and as will be appreciated by one of skill in the art, and with the help of this disclosure, in some aspects, the redox agent (D) can comprise two or more redox elements, such as manganese (Mn), and tungsten (W), for example; or manganese (Mn), tungsten (W), and praseodymium (Pr), as another example; etc.

In an aspect, the second rare earth element (E) and/or the third rare earth element (D) can be basic (e.g., can exhibit some degree of basicity; can have affinity for hydrogen; can exhibit some degree of affinity for hydrogen). Nonlimiting examples of rare earth elements that can be considered basic for purposes of the disclosure herein include lanthanum (La), scandium (Sc), cerium (Ce), praseodymium (Pr), neodymium (Nd), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof. As will be appreciated by one of skill in the art, and with the help of this disclosure, and without wishing to be limited by theory, the OCM reaction is a multi-step reaction, wherein each step of the OCM reaction could benefit from specific OCM catalytic properties. For example, and without wishing to be limited by theory, an OCM catalyst should exhibit some degree of basicity to abstract a hydrogen from $CH_4$ to form hydroxyl groups [OH] on the OCM catalyst surface, as well as methyl radicals ($CH_{3*}$). Further, and without wishing to be limited by theory, an OCM catalyst should exhibit oxidative properties for the OCM catalyst to convert the hydroxyl groups [OH] from the catalyst surface to water, which can allow for the OCM reaction to continue (e.g., propagate). Furthermore, as will be appreciated by one of skill in the art, and with the help of this disclosure, and without wishing to be limited by theory, an OCM catalyst could also benefit from properties like oxygen ion conductivity and proton conductivity, which properties can be critical for the OCM reaction to proceed at a very high rate (e.g., its highest possible rate). Furthermore, as will be appreciated by one of skill in the art, and with the help of this disclosure, and without wishing to be limited by theory, an OCM catalyst comprising a single metal might not provide all the necessary properties for an optimum OCM reaction (e.g., best OCM reaction outcome) at the best level, and as such conducting an optimum OCM reaction may require an OCM catalyst with tailored composition in terms of metals present, wherein the different metals can have optimum properties for various OCM reaction steps, and wherein the different metals can provide synergistically for achieving the best performance for the OCM catalyst in an OCM reaction.

In an aspect, the OCM nanoplate catalyst composition as disclosed herein can comprise one or more oxides of A; one or more oxides of Z; one or more oxides of E; one or more oxides of D; or combinations thereof. The OCM nanoplate catalyst composition can comprise one or more oxides of a metal, wherein the metal comprises A, Z, and optionally E and/or D. In some aspects, the OCM nanoplate catalyst composition can comprise, consist of, or consist essentially of the one or more oxides.

In an aspect, the one or more oxides can be present in the OCM nanoplate catalyst composition in an amount of from about 0.01 wt. % to about 100.0 wt. %, alternatively from about 0.1 wt. % to about 99.0 wt. %, alternatively from about 1.0 wt. % to about 95.0 wt. %, alternatively from about 10.0 wt. % to about 90.0 wt. %, or alternatively from about 30.0 wt. % to about 70.0 wt. %, based on the total weight of the OCM nanoplate catalyst composition. As will be appreciated by one of skill in the art, and with the help of this disclosure, a portion of the one or more oxides, in the presence of water, such as atmospheric moisture, can convert to hydroxides, and it is possible that the OCM nanoplate catalyst composition will comprise some hydroxides, due to exposing the OCM nanoplate catalyst composition comprising the one or more oxides to water (e.g., atmospheric moisture). Further, as will be appreciated by one of skill in the art, and with the help of this disclosure, a portion of the one or more oxides, in the presence of carbon dioxide, such as atmospheric carbon dioxide, can convert to carbonates, and it is possible that the OCM nanoplate catalyst composition will comprise some carbonates, due to exposing the OCM nanoplate catalyst composition comprising the one or more oxides to carbon dioxide (e.g., atmospheric carbon dioxide).

In an aspect, an OCM nanoplate catalyst composition suitable for use in the present disclosure can comprise one or more oxides, wherein the one or more oxides can comprise a single metal oxide, mixtures of single metal oxides, a mixed metal oxide, mixtures of mixed metal oxides, mixtures of single metal oxides and mixed metal oxides, or combinations thereof.

The single metal oxide comprises one metal selected from the group consisting of A, Z, E, and D. A single metal oxide can be characterized by the general formula $M_m O_y$; wherein M is the metal selected from the group consisting of A, Z, E, and D; and wherein m and y are integers from 1 to 7, alternatively from 1 to 5, or alternatively from 1 to 3. A single metal oxide contains one and only one metal cation. Nonlimiting examples of single metal oxides suitable for use in the OCM nanoplate catalyst composition of the present disclosure include CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $W_2O_3$, $SnO_2$, and the like, or combinations thereof.

In an aspect, mixtures of single metal oxides can comprise two or more different single metal oxides, wherein the two or more different single metal oxides have been mixed together to form the mixture of single metal oxides. Mixtures of single metal oxides can comprise two or more different single metal oxides, wherein each single metal oxide can be selected from the group consisting of CaO, MgO, SrO, BaO, $La_2O_3$, $Sc_2O_3$, $Y_2O_3$, $CeO_2$, $Ce_2O_3$, $Pr_2O_3$, $PrO_2$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Lu_2O_3$, $Yb_2O_3$, $Tm_2O_3$, $WO_3$, $MnO_2$, $WO_2O_3$, and $SnO_2$. Nonlimiting examples of mixtures of single metal oxides suitable for use in the OCM nanoplate catalyst composition of the present disclosure include SrO—$La_2O_3$, SrO—MgO—$La_2O_3$, SrO—$Yb_2O_3$—$La_2O_3$, SrO—$Er_2O_3$—$La_2O_3$, SrO—$CeO_2$—$La_2O_3$, SrO—$MnO_2$—$La_2O_3$, SrO—$WO_3$—$W_2O_3$—$La_2O_3$, SrO—$WO_3$—$Tm_2O_3$—$La_2O_3$, SrO—$WO_3$—$Tm_2O_3$—$La_2O_3$, SrO—BaO—$CeO_2$—$Er_2O_3$—$La_2O_3$, SrO—$CeO_2$—$Ce_2O_3$—$Er_2O_3$—$La_2O_3$, SrO—BaO—$WO_3$—$W_2O_3$—$La_2O_3$, SrO—BaO—$Sm_2O_3$—$WO_3$—$W_2O_3$—$La_2O_3$, SrO—MgO—$CeO_2$—$Ce_2O_3$—$WO_3$—$W_2O_3$—$La_2O_3$, SrO—CaO—$PrO_2$—$Pr_2O_3$—MnO—$Mn_2O_3$—$La_2O_3$, and the like, or combinations thereof.

The mixed metal oxide comprises two or more different metals, wherein each metal can be independently selected from the group consisting of A, Z, E, and D. A mixed metal oxide can be characterized by the general formula $M^1_{m1} M^2_{m2} O_y$; wherein $M^1$ and $M^2$ are metals; wherein each of the $M^1$ and $M^2$ can be independently selected from the group consisting of A, Z, E, and D; and wherein m1, m2 and are integers from 1 to 15, alternatively from 1 to 10, or alternatively from 1 to 7. In some aspects, $M^1$ and $M^2$ can be metal cations of different chemical elements, for example $M^1$ can be a lanthanum cation and $M^2$ can be a strontium cation. In other aspects, $M^1$ and $M^2$ can be different cations of the same chemical element, wherein $M^1$ and $M^2$ can have different oxidation states. For example, the mixed metal oxide can comprise $Mn_3O_4$, wherein $M^1$ can be a Mn (II) cation and $M^2$ can be a Mn (III) cation. Nonlimiting examples of mixed metal oxides suitable for use in the OCM nanoplate catalyst composition of the present disclosure include La/SrO; $LaYbO_3$; $SrYb_2O_4$; $Sr_2CeO_4$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of mixed metal oxides can comprise two or more different mixed metal oxides, wherein the two or more different mixed metal oxides have been mixed together to form the mixture of mixed metal oxides. Mixtures of mixed metal oxides can comprise two or more different mixed metal oxides, such as La/SrO; $LaYbO_3$; $SrYb_2O_4$; $Sr_2CeO_{04}$; $Mn_3O_4$; La/MgO; $Sm_2Ce_2O_7$; $Er_2Ce_2O_7$; $CaTm_2O_4$; $MgYb_2O_4$; $SrCe_{(1-y)}Yb_yO_3$, wherein y can be from about 0.01 to about 0.99; and the like; or combinations thereof.

In an aspect, mixtures of single metal oxides and mixed metal oxides can comprise at least one single metal oxide and at least one mixed metal oxide, wherein the at least one single metal oxide and the at least one mixed metal oxide have been mixed together to form the mixture of single metal oxides and mixed metal oxides.

The OCM nanoplate catalyst composition suitable for use in the present disclosure can be supported OCM nanoplate catalyst compositions and/or unsupported OCM nanoplate catalyst compositions. In some aspects, the supported OCM nanoplate catalyst composition can comprise a support, wherein the support can be catalytically active (e.g., the support can catalyze an OCM reaction, such as MgO). In other aspects, the supported OCM nanoplate catalyst composition can comprise a support, wherein the support can be catalytically inactive (e.g., the support cannot catalyze an OCM reaction, such as $SiO_2$). In yet other aspects, the supported OCM nanoplate catalyst composition can comprise a catalytically active support and a catalytically inactive support. Nonlimiting examples of a support suitable for use in the present disclosure include MgO, $Al_2O_3$, $SiO_2$, $ZrO_2$, $TiO_2$, and the like, or combinations thereof. As will be appreciated by one of skill in the art, and with the help of this disclosure, the support can be purchased or can be prepared by using any suitable methodology, such as for example precipitation/co-precipitation, sol-gel techniques, templates/surface derivatized metal oxides synthesis, solid-state synthesis of mixed metal oxides, microemulsion techniques, solvothermal techniques, sonochemical techniques, combustion synthesis, etc.

In an aspect, the OCM nanoplate catalyst composition can further comprise a support, wherein at least a portion of the OCM nanoplate catalyst composition contacts, coats, is embedded in, is supported by, and/or is distributed throughout at least a portion of the support. In such aspect, the support can be in the form of powders, particles, pellets, monoliths, foams, honeycombs, and the like, or combinations thereof. Nonlimiting examples of support particle shapes include cylindrical, discoidal, spherical, tabular, ellipsoidal, equant, irregular, cubic, acicular, and the like, or combinations thereof.

A supported OCM nanoplate catalyst composition can have any suitable desired particle specifications, for example as required by a specific application.

In an aspect, the OCM nanoplate catalyst composition can further comprise a porous support. As will be appreciated by one of skill in the art, and with the help of this disclosure, a porous material (e.g., support) can provide for a further enhanced surface area of contact between the OCM nanoplate catalyst composition and a reactant mixture, which in turn would result in a higher $CH_4$ conversion to $CH_{3*}$. Further, as will be appreciated by one of skill in the art, and with the help of this disclosure, and without wishing to be limited by theory, the support (e.g., porous support) should have a suitable pore volume (e.g., a fairly large pore volume) that allows for a sufficient amount of catalyst to be loaded onto the support, thereby reducing the mass transfer resistance for the reaction.

The OCM nanoplate catalyst composition as disclosed herein can be made by using any suitable methodology. In an aspect, a method of making an OCM nanoplate catalyst composition can comprise a step of forming an OCM nanoplate catalyst precursor mixture; wherein the OCM nanoplate catalyst precursor mixture comprises a nitrate comprising an alkaline earth metal (A) cation, a nitrate comprising a first rare earth element (Z) cation, a nitrate comprising a second rare earth element (E) cation, and a nitrate comprising a redox agent cation or a third rare earth element (D) cation; and wherein the first rare earth element cation, the second rare earth element cation, and the third rare earth element cation, when present, are not the same (i.e., are different). The OCM nanoplate catalyst precursor mixture is characterized by a molar ratio of first rare earth element to alkaline earth metal of b:1, wherein b is from about 1.0 to about 3.0, alternatively from about 1.25 to about 2.75, or alternatively from about 1.5 to about 2.5. The OCM nanoplate catalyst precursor mixture is characterized by a molar ratio of second rare earth element to alkaline earth metal of c:1, wherein c is from about 0 to about 1.5, alternatively from about 0.1 to about 1.25, or alternatively from about 0.5 to about 1.0. The OCM nanoplate catalyst precursor mixture is characterized by a molar ratio of redox agent or third rare earth element to alkaline earth metal of d:1, wherein d is from about 0 to about 1.5, alternatively from about 0.1 to about 1.25, or alternatively from about 0.5 to about 1.0. b is greater than the sum of c and d (b>(c+d)).

In an aspect, the step of forming the OCM nanoplate catalyst precursor mixture can comprise solubilizing the nitrate comprising an alkaline earth metal cation, the nitrate comprising a first rare earth element cation, the nitrate comprising a second rare earth element cation, and the nitrate comprising a redox agent cation or a third rare earth element cation in an aqueous medium to form an OCM nanoplate catalyst precursor aqueous solution. The aqueous medium can be water, or an aqueous solution. The OCM nanoplate catalyst precursor aqueous solution can be formed by dissolving the nitrate comprising an alkaline earth metal cation, the nitrate comprising a first rare earth element cation, the nitrate comprising a second rare earth element cation, the nitrate comprising a redox agent cation or a third rare earth element cation, or combinations thereof, in water or any suitable aqueous medium. As will be appreciated by one of skill in the art, and with the help of this disclosure, the nitrate comprising an alkaline earth metal cation, the nitrate comprising a first rare earth element cation, the nitrate comprising a second rare earth element cation, and the nitrate comprising a redox agent cation or a third rare earth element cation can be dissolved in an aqueous medium in any suitable order. In some aspects, the nitrate comprising an alkaline earth metal cation, the nitrate comprising a first rare earth element cation, the nitrate comprising a second rare earth element cation, and the nitrate comprising a redox agent cation or a third rare earth element cation can be first mixed together and then dissolved in an aqueous medium.

The OCM nanoplate catalyst precursor aqueous solution can be dried to form the OCM nanoplate catalyst precursor mixture. In an aspect, at least a portion of the OCM nanoplate catalyst precursor aqueous solution can be dried at a temperature of equal to or greater than about 75° C., alternatively of equal to or greater than about 100° C., or alternatively of equal to or greater than about 125° C., to yield the OCM nanoplate catalyst precursor mixture. The OCM nanoplate catalyst precursor aqueous solution can be dried for a time period of equal to or greater than about 4 hours, alternatively equal to or greater than about 8 hours, or alternatively equal to or greater than about 12 hours.

In an aspect, a method of making an OCM nanoplate catalyst composition can comprise a step of calcining at least a portion of the OCM nanoplate catalyst precursor mixture to form the OCM nanoplate catalyst composition, wherein the OCM nanoplate catalyst composition is characterized by the general formula $A_aZ_bE_cD_dO_x$; wherein A is an alkaline earth metal; wherein Z is a first rare earth element; wherein E is a second rare earth element; wherein D is a redox agent or a third rare earth element; wherein the first rare earth element, the second rare earth element, and the third rare earth element, when present, are not the same; wherein a is 1.0; wherein b is from about 1.0 to about 3.0; wherein c is from about 0 to about 1.5; wherein d is from about 0 to about 1.5; wherein b is greater than the sum of c and d (b>(c+d)); and wherein x balances the oxidation states. The OCM nanoplate catalyst precursor mixture can be calcined at a temperature of equal to or greater than about 750° C., alternatively equal to or greater than about 800° C., or alternatively equal to or greater than about 900° C., to yield the OCM nanoplate catalyst composition. The OCM nanoplate catalyst precursor mixture can be calcined for a time period of equal to or greater than about 2 hours, alternatively equal to or greater than about 4 hours, or alternatively equal to or greater than about 6 hours.

In some aspects, at least a portion of the OCM nanoplate catalyst precursor mixture can be calcined in an oxidizing atmosphere (e.g., in an atmosphere comprising oxygen, for example in air) to form the OCM nanoplate catalyst composition. Without wishing to be limited by theory, the oxygen in the OCM nanoplate catalyst compositions characterized by the general formula $A_aZ_bE_cD_dO_x$ can originate in the oxidizing atmosphere used for calcining the OCM nanoplate catalyst precursor mixture. Further, without wishing to be limited by theory, the oxygen in the OCM nanoplate catalyst compositions characterized by the general formula $A_aZ_bE_cD_dO_x$ can originate in the nitrate comprising an alkaline earth metal cation, the nitrate comprising a first rare earth element cation, the nitrate comprising a second rare earth element cation, and the nitrate comprising a redox agent cation or a third rare earth element cation.

In some aspects, the method of making an OCM nanoplate catalyst composition can further comprise contacting the OCM nanoplate catalyst composition with a support to yield a supported catalyst (e.g., a supported OCM nanoplate catalyst, a supported OCM nanoplate catalyst composition, etc.).

In other aspects, the method of making an OCM nanoplate catalyst composition can comprise forming the OCM nanoplate catalyst composition in the presence of the support, such that the resulting OCM nanoplate catalyst composition (after the calcining step) comprises the support. For example, at least a portion of the OCM nanoplate catalyst precursor aqueous solution can be contacted with a support to yield a supported OCM nanoplate catalyst precursor. In an aspect, at least a portion of the supported OCM nanoplate catalyst precursor can be further dried (e.g., at a temperature of equal to or greater than about 75° C.) and calcined (e.g., at a temperature of equal to or greater than about 750° C.) to form the OCM nanoplate catalyst composition.

In an aspect, a method for producing olefins as disclosed herein can comprise (a) introducing a reactant mixture (e.g., OCM reactant mixture) to an OCM reactor comprising the OCM nanoplate catalyst composition as disclosed herein, wherein the reactant mixture comprises methane ($CH_4$) and oxygen ($O_2$); and (b) allowing at least a portion of the reactant mixture to contact at least a portion of the OCM nanoplate catalyst composition and react via an OCM reaction to form a product mixture comprising unreacted methane and olefins.

The OCM reactant mixture can be a gaseous mixture. The OCM reactant mixture can comprise a hydrocarbon or mixtures of hydrocarbons, and oxygen. In some aspects, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons such as diesel fuel, jet fuel, gasoline, tars, kerosene, etc.), oxygenated hydrocarbons, biodiesel, alcohols, dimethyl ether, and the like, or combinations thereof. In an aspect, the OCM reactant mixture can comprise $CH_4$ and $O_2$.

The $O_2$ used in the OCM reactant mixture can be oxygen gas (which may be obtained via a membrane separation process), technical oxygen (which may contain some air), air, oxygen enriched air, and the like, or combinations thereof.

The OCM reactant mixture can further comprise a diluent. The diluent is inert with respect to the OCM reaction, e.g., the diluent does not participate in the OCM reaction. In an aspect, the diluent can comprise water (e.g., steam), nitrogen, inert gases, and the like, or combinations thereof. In an aspect, the diluent can be present in the OCM reactant mixture in an amount of from about 0.5% to about 80%, alternatively from about 5% to about 50%, or alternatively from about 10% to about 30%, based on the total volume of the OCM reactant mixture.

The OCM reactor can comprise an adiabatic reactor, an autothermal reactor, an isothermal reactor, a tubular reactor, a cooled tubular reactor, a continuous flow reactor, a fixed bed reactor, a fluidized bed reactor, a moving bed reactor, and the like, or combinations thereof. In an aspect, the OCM reactor can comprise a catalyst bed comprising the OCM nanoplate catalyst composition.

The OCM reaction mixture can be introduced to the OCM reactor at a temperature of from about 150° C. to about 1,000° C., alternatively from about 225° C. to about 900° C., or alternatively from about 250° C. to about 800° C. As will be appreciated by one of skill in the art, and with the help of this disclosure, while the OCM reaction is exothermic, heat input is necessary for promoting the formation of methyl radicals from $CH_4$, as the C—H bonds of $CH_4$ are very stable, and the formation of methyl radicals from $CH_4$ is endothermic. In an aspect, the OCM reaction mixture can be introduced to the OCM reactor at a temperature effective to promote an OCM reaction.

The OCM reactor can be characterized by a temperature of from about 400° C. to about 1,200° C., alternatively from about 500° C. to about 1,100° C., or alternatively from about 600° C. to about 1,000° C.

The OCM reactor can be characterized by a pressure of from about ambient pressure (e.g., atmospheric pressure) to about 500 psig, alternatively from about ambient pressure to about 200 psig, or alternatively from about ambient pressure to about 150 psig. In an aspect, the method for producing olefins as disclosed herein can be carried out at ambient pressure.

The OCM reactor can be characterized by a gas hourly space velocity (GHSV) of from about 500 $h^{-1}$ to about 10,000,000 $h^{-1}$, alternatively from about 500 $h^{-1}$ to about 1,000,000 $h^{-1}$, alternatively from about 500 $h^{-1}$ to about 100,000 $h^{-1}$, alternatively from about 500 $h^{-1}$ to about 50,000 $h^{-1}$, alternatively from about 1,000 $h^{-1}$ to about 40,000 $h^{-1}$, or alternatively from about 1,500 $h^{-1}$ to about 25,000 $h^{-1}$. Generally, the GHSV relates a reactant (e.g., reactant mixture) gas flow rate to a reactor volume. GHSV is usually measured at standard temperature and pressure.

In an aspect, the method for producing olefins as disclosed herein can comprise recovering at least a portion of the product mixture from the OCM reactor, wherein the product mixture can comprise olefins, water, CO, $CO_2$, and unreacted methane. In an aspect, a method for producing olefins as disclosed herein can comprise recovering at least a portion of the olefins from the product mixture. The product mixture can comprise $C_{2+}$ hydrocarbons (including olefins), unreacted methane, and optionally a diluent. The $C_{2+}$ hydrocarbons can comprise $C_2$ hydrocarbons and $C_3$ hydrocarbons. In an aspect, the $C_{2+}$ hydrocarbons can further comprise $C_4$ hydrocarbons ($C_4s$), such as for example butane, iso-butane, n-butane, butylene, etc. The $C_2$ hydrocarbons can comprise ethylene ($C_2H_4$) and ethane ($C_2H_6$). The $C_2$ hydrocarbons can further comprise acetylene ($C_2H_2$). The $C_3$ hydrocarbons can comprise propylene ($C_3H_6$) and propane ($C_3H_8$).

The water produced from the OCM reaction and the water used as a diluent (if water diluent is used) can be separated from the product mixture prior to separating any of the other product mixture components. For example, by cooling down the product mixture to a temperature where the water condenses (e.g., below 100° C. at ambient pressure), the water can be removed from the product mixture, by using a flash chamber for example.

A method for producing olefins as disclosed herein can comprise recovering at least a portion of the olefins from the product mixture. In an aspect, at least a portion of the olefins can be separated from the product mixture by distillation (e.g., cryogenic distillation). As will be appreciated by one of skill in the art, and with the help of this disclosure, the olefins are generally individually separated from their paraffin counterparts by distillation (e.g., cryogenic distillation). For example, ethylene can be separated from ethane by distillation (e.g., cryogenic distillation). As another example, propylene can be separated from propane by distillation (e.g., cryogenic distillation).

In an aspect, at least a portion of the unreacted methane can be separated from the product mixture to yield recovered methane. Methane can be separated from the product mixture by using any suitable separation technique, such as for example distillation (e.g., cryogenic distillation). At least a portion of the recovered methane can be recycled to the reactant mixture.

In an aspect, the $O_2$ conversion of the OCM reaction as disclosed herein can be equal to or greater than about 90%, alternatively equal to or greater than about 95%, alternatively equal to or greater than about 99%, alternatively equal to or greater than about 99.9%, or alternatively about 100%. Generally, a conversion of a reagent or reactant refers to the percentage (usually mol %) of reagent that reacted to both undesired and desired products, based on the total amount (e.g., moles) of reagent present before any reaction took place. For purposes of the disclosure herein, the conversion of a reagent is a % conversion based on moles converted. As will be appreciated by one of skill in the art, and with the help of this disclosure, the reactant mixture in OCM reactions is generally characterized by a methane to oxygen molar ratio of greater than 1:1, and as such the $O_2$ conversion is fairly high in OCM processes, most often approaching 90%-100%. Without wishing to be limited by theory, oxygen is usually a limiting reagent in OCM processes. The oxygen conversion can be calculated by using equation (6):

$$O_2 \text{ conversion} = \frac{O_2^{in} - O_2^{out}}{O_2^{in}} \times 100\% \qquad (6)$$

wherein $O_2^{in}$=number of moles of $O_2$ that entered the OCM reactor as part of the reactant mixture; and $O_2^{out}$=number of moles of $O_2$ that was recovered from the OCM reactor as part of the product mixture.

In an aspect, the OCM nanoplate catalyst composition is characterized by an activity increase; wherein the activity increase is defined as a decrease in a reactor temperature effective for achieving an $O_2$ conversion of equal to or greater than about 90%. In such aspect, the reactor temperature effective for achieving an $O_2$ conversion of equal to or greater than about 90% of the OCM nanoplate catalyst composition is decreased by equal to or greater than about 25° C., alternatively by equal to or greater than about 50° C., alternatively by equal to or greater than about 75° C., or alternatively by equal to or greater than about 100° C., when compared to a reactor temperature effective for achieving an $O_2$ conversion of equal to or greater than about 90% of an otherwise similar OCM catalyst composition comprising less than about 25 wt. % nanoplates, based on the total weight of the composition.

In some aspects, the OCM nanoplate catalyst composition as disclosed herein can be characterized by a reactor temperature effective for achieving an $O_2$ conversion of equal to or greater than about 90% of less than about 700° C., alternatively less than about 650° C., or alternatively less than about 600° C. As will be appreciated by one of skill in the art, and with the help of this disclosure, the reactor temperature effective for achieving an $O_2$ conversion of equal to or greater than about 90% is dependent upon specific reactor conditions, such as for example methane to oxygen molar ratio, type and size of reactor, GHSV, etc.

In an aspect, the OCM nanoplate catalyst composition as disclosed herein can be characterized by a $C_{2+}$ selectivity that is increased when compared to a $C_{2+}$ selectivity of an otherwise similar OCM catalyst composition comprising less than about 25 wt. % nanoplates, based on the total weight of the composition.

Generally, a selectivity to a desired product or products refers to how much desired product was formed divided by the total products formed, both desired and undesired. For purposes of the disclosure herein, the selectivity to a desired product is a % selectivity based on moles converted into the desired product. Further, for purposes of the disclosure herein, a $C_x$ selectivity (e.g., $C_2$ selectivity, $C_{2+}$ selectivity, etc.) can be calculated by dividing a number of moles of carbon (C) from $CH_4$ that were converted into the desired product (e.g., $C_{C2H4}$, $C_{C2H6}$, etc.) by the total number of moles of C from $CH_4$ that were converted (e.g., $C_{C2H4}$, $C_{C2H6}$, $C_{C2H2}$, $C_{C3H6}$, $C_{C3H8}$, $C_{C4s}$, $C_{CO2}$, $C_{CO}$, etc.). $C_{C2H4}$=number of moles of C from $CH_4$ that were converted into $C_2H_4$; $C_{C2H6}$=number of moles of C from $CH_4$ that were converted into $C_2H_6$; $C_{C2H2}$=number of moles of C from $CH_4$ that were converted into $C_2H_2$; $C_{C3H6}$=number of moles of C from $CH_4$ that were converted into $C_3H_6$; $C_{C3H8}$=number of moles of C from $CH_4$ that were converted into $C_3H_8$; $C_{C4s}$=number of moles of C from $CH_4$ that were converted into $C_4$ hydrocarbons ($C_4$s); $C_{CO2}$=number of moles of C from $CH_4$ that were converted into $CO_2$; $C_{CO}$=number of moles of C from $CH_4$ that were converted into CO; etc.

A $C_{2+}$ selectivity (e.g., selectivity to $C_{2+}$ hydrocarbons) refers to how much $C_2H_4$, $C_3H_6$, $C_2H_2$, $C_2H_6$, $C_3H_8$, and $C_4$s were formed divided by the total products formed, including $C_2H_4$, $C_3H_6$, $C_2H_2$, $C_2H_6$, $C_3H_8$, $C_4$s, $CO_2$ and CO. For example, the $C_{2+}$ selectivity can be calculated by using equation (7):

$$C_{2+} \text{ selectivity} = \qquad (7)$$
$$\frac{2C_{C_2H_4} + 2C_{C_2H_6} + 2C_{C_2H_2} + 3C_{C_3H_6} + 3C_{C_3H_8} + 4C_{C_{4s}}}{2C_{C_2H_4} + 2C_{C_2H_6} + 2C_{C_2H_2} + 3C_{C_3H_6} +} \times 100\%$$
$$3C_{C_3H_8} + 4C_{C_{4s}} + C_{CO_2} + C_{CO}$$

As will be appreciated by one of skill in the art, and with the help of this disclosure, if a specific product and/or hydrocarbon product is not produced in a certain OCM reaction/process, then the corresponding $C_{Cx}$ is 0, and the term is simply removed from selectivity calculations.

In an aspect, the method for producing olefins as disclosed herein can further comprise minimizing deep oxidation of methane to $CO_x$ products, such as carbon monoxide (CO) and/or carbon dioxide ($CO_2$). Without wishing to be limited by theory, when the selectivity to desired products (e.g., $C_{2+}$ selectivity) of an OCM process increases, less methane is converted to undesirable products, such as deep oxidation products (e.g., CO, $CO_2$), which in turn means that more oxygen (which is often the limiting reagent in OCM processes) is available for the conversion of methane to desirable products (e.g., $C_2$ products, $C_2H_4$, $C_{2+}$ products, etc.), thus enabling an increased yield of desired $C_{2+}$ products.

In an aspect, the OCM nanoplate catalyst composition as disclosed herein can be characterized by a $CO_2$ selectivity that is decreased by equal to or greater than about 5%, alternatively equal to or greater than about 10%, or alternatively equal to or greater than about 15% when compared to a $CO_2$ selectivity of an otherwise similar OCM catalyst composition comprising less than about 25 wt. % nanoplates, based on the total weight of the composition.

In an aspect, the OCM nanoplate catalyst composition as disclosed herein comprises equal to or greater than about 25 wt. % nanoplates, based on the total weight of the OCM nanoplate catalyst composition; wherein a nanoplate is a three-dimensional object defined in accordance with ISO/TS 80004-2:2015; wherein the thickness (t) of the nanoplate is t≤100 nm; wherein the length (l) of the nanoplate is l>t; wherein the width (w) of the nanoplate is w>t; wherein (i) l≥5 t, (ii) w≥5 t, or (iii) l≥5 t and w≥5 t; and wherein the OCM nanoplate catalyst composition can be characterized by the general formula $A_aLa_bE_cO_x$; wherein E is a second rare earth element; wherein a is 1.0; wherein b is from about 1.0 to about 3.0, alternatively from about 1.25 to about 2.75, or alternatively from about 1.5 to about 2.5; wherein c is from about 0.01 to about 1.5, alternatively from about 0.1 to about 1.25, or alternatively from about 0.5 to about 1.0; wherein b is greater than c (b>c); and wherein x balances the oxidation states. As will be appreciated by one of the skill in the art, and with the help of this disclosure, at least some of the Sr, La, and E can have multiple oxidation states within the OCM nanoplate catalyst composition, and as such x can have any suitable value that allows for the oxygen anions to balance all the cations.

In an aspect of the OCM nanoplate catalyst composition characterized by the general formula $A_aLa_bE_cO_x$, A is Sr, and E is Yb. In such aspect, the OCM nanoplate catalyst composition comprises equal to or greater than about 25 wt. % nanoplates, based on the total weight of the OCM nanoplate catalyst composition; wherein a nanoplate is a three-dimensional object defined in accordance with ISO/TS 80004-2:2015; wherein the thickness (t) of the nanoplate is t≤100 nm; wherein the length (l) of the nanoplate is l>t; wherein the width (w) of the nanoplate is w>t; wherein (i) l≥5 t, (ii) w≥5 t, or (iii) l≥5 t and w≥5 t; and wherein the OCM nanoplate catalyst composition can be characterized by the general formula $Sr_aLa_bYb_cO_x$; wherein a is 1.0; wherein b is from about 1.0 to about 3.0, alternatively from about 1.25 to about 2.75, or alternatively from about 1.5 to about 2.5; wherein c is from about 0.01 to about 1.5, alternatively from about 0.1 to about 1.25, or alternatively from about 0.5 to about 1.0; wherein b is greater than c; and wherein x balances the oxidation states.

In another aspect, the OCM nanoplate catalyst composition as disclosed herein comprises equal to or greater than about 25 wt. % nanoplates, based on the total weight of the OCM nanoplate catalyst composition; wherein a nanoplate is a three-dimensional object defined in accordance with ISO/TS 80004-2:2015; wherein the thickness (t) of the nanoplate is t≤100 nm; wherein the length (l) of the nanoplate is l>t; wherein the width (w) of the nanoplate is w>t; wherein (i) l≥5 t, (ii) w≥5 t, or (iii) l≥5 t and w≥5 t; and wherein the OCM nanoplate catalyst composition can be characterized by the general formula $Sr_aLa_{b1}Nd_{b2}Yb_cO_x$; wherein a is 1.0; wherein b1 is from about 0.01 to about 2.99, alternatively from about 0.1 to about 2.75, or alternatively from about 1 to about 2.5; wherein b2 is from about 0.01 to about 2.99, alternatively from about 0.1 to about 2.75, or alternatively from about 1 to about 2.5; wherein b=(b1+b2); wherein b is from about 1.0 to about 3.0, alternatively from about 1.25 to about 2.75, or alternatively from about 1.5 to about 2.5; wherein c is from about 0.01 to about 1.5, alternatively from about 0.1 to about 1.25, or alternatively from about 0.5 to about 1.0; wherein b is greater than c; and wherein x balances the oxidation states. As will be appreciated by one of the skill in the art, and with the help of this disclosure, at least some of the Sr, La, Nd, and Yb can have multiple oxidation states within the OCM nanoplate catalyst composition, and as such x can have any suitable value that allows for the oxygen anions to balance all the cations.

In an aspect, the OCM nanoplate catalyst composition, and methods of making and using same, as disclosed herein can advantageously display improvements in one or more catalyst characteristics when compared to conventional OCM catalysts, e.g., OCM catalysts comprising less than about 25 wt. % nanoplates, based on the total weight of the composition. In the case of conventional OCM catalysts, if the reaction (e.g., OCM reaction) is mass transfer controlled by diffusion resistance or hindrances due to low porosity, the apparent activity of the conventional OCM catalyst will be significantly lower than its intrinsic activity. The OCM nanoplate catalyst composition as disclosed herein advantageously displays an increased number of catalytically active sites, when compared to conventional OCM catalysts.

The OCM nanoplate catalyst composition as disclosed herein advantageously provides for a physical catalyst structure that displays low diffusion resistance or hindrance, for example when compared to an otherwise similar OCM catalyst comprising less than about 25 wt. % nanoplates, based on the total weight of the composition. Without wishing to be limited by theory, the increased porosity of the OCM nanoplate catalyst composition as disclosed herein allows methyl radicals to leave the catalyst surface more easily, thereby providing the methyl radicals with fewer chances to be re-adsorbed and be oxidized. Furthermore, and without wishing to be limited by theory, the increase in surface area of the OCM nanoplate catalyst composition as disclosed herein provides more opportunity for interaction of the reactants with active sites, which further benefits catalyst activity.

The OCM nanoplate catalyst composition as disclosed herein can advantageously be cost effective and/or commercially feasible. Additional advantages of the OCM nanoplate catalyst compositions characterized by the general formula $A_aZ_bE_cD_dO_x$, as disclosed herein; and methods of making and using same, can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Performance testing. The catalysts were performance tested in a 2.3 mm ID quartz tube reactor. The reactor was loaded with 20 mg of catalyst. A mixture of methane and oxygen at a fixed $CH_4:O_2$ ratio of 7.4 was fed to the reactor at a total flow rate of 40.0 sccm. Products obtained were analyzed by using online GC with TCD and FID detectors.

Scanning Electron Microscope (SEM) imaging. The SEM images of the catalysts are obtained by using JEOL 7800F.

Example 1

Oxidative coupling of methane (OCM) catalyst compositions were prepared as follows. Catalyst #1 $(Sr_{1.0}La_{1.2}Yb_{0.1}O_x)$ was prepared with the following preparation method. To get 10 g of $Sr_{0.1}La_{1.2}Yb_{0.1}O_x$, 4.03 g of $Sr(NO_3)_2$, 10.41 g of $La(NO_3)_3 \cdot 6H_2O$, and 0.86 g of $Yb(NO_3)_3 \cdot 5H_2O$ were mixed and dissolved into 25 ml water. The obtained mixture was dried at 125° C. overnight. The dried material was then calcined at 900° C. for 6 hours to produce the catalyst #1.

With the same preparation method and with different raw materials, other catalysts (#2, #3, #4, #5, #6, and #7) and comparative example (reference) catalysts (comparative catalysts #2, #3, and #4) were prepared.

Example 2

The performance and properties of catalyst #1 were investigated.

Figure 2:
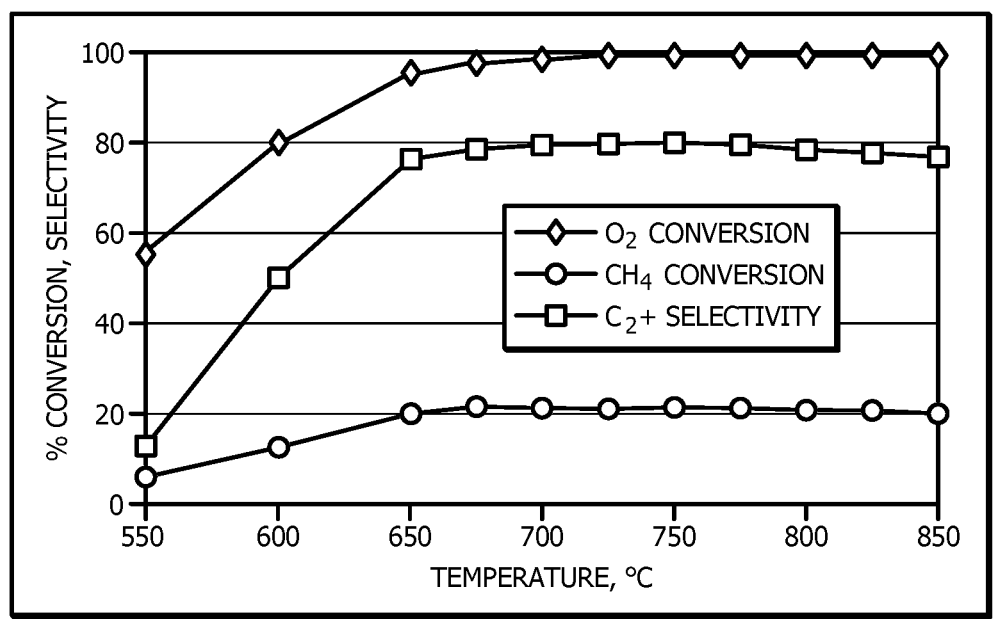
FIG. 2 displays a graph of $C_{2+}$ selectivity, oxygen conversion, and methane conversion as a function of temperature for an oxidative coupling of methane (OCM) nanoplate catalyst composition in an OCM reaction.

The performance of catalyst #1 $(Sr_{1.0}La_{1.2}Yb_{0.1}O_x)$ is shown in FIG. 2, in terms of $O_2$ conversion, $CH_4$ conversion, and $C_{2+}$ selectivity $(S_{C2+})$. The $CH_4$ conversion can be calculated by using equation (8):

$$CH_4 = \frac{C_{CH_4}^{in} - C_{CH_4}^{out}}{C_{CH_4}^{in}} \times 100\% \qquad (8)$$

wherein $C_{CH_4}^{in}$=number of moles of C from $CH_4$ that entered the reactor as part of the reactant mixture; and $C_{CH_4}^{out}$=number of moles of C from $CH_4$ that was recovered from the reactor as part of the product mixture.

The performance of catalyst #1 under different reactor temperatures is shown FIG. 2. It can be seen that this catalyst reaches 90% or higher oxygen conversion at 650° C., indicating a very high activity. In the following examples/results, this temperature will be used to compare the activity between different catalysts, as shown in Table 1.

TABLE 1

Performance of different catalysts

| | | Nanoplate Dimensions l, w and t | | Temperature to achieve 90%+ $O_2$ | $S_{C_{2+}}$ |
|---|---|---|---|---|---|
| | Catalyst composition | t (nm) | (l or w)/t | conversion (° C.) | (%) |
| Catalyst #1 | $Sr_{1.0}La_{1.2}Yb_{0.1}O_x$ | 100 | >5 | 650 | 80.2 |
| Catalyst #1 | $Sr_{1.0}La_{1.2}Yb_{0.1}O_x$ | 100 | >5 | 700* | 80.3 |
| Catalyst #2 | $Sr_{1.0}La_{1.8}Yb_{0.1}O_x$ | 100 | >5 | 650* | 80.2 |
| Catalyst #3 | $Sr_{1.0}La_{0.9}Yb_{0.1}Nd_{0.1}O_x$ | 100 | >5 | 650 | 80.2 |
| Catalyst #4 | $Sr_{1.0}La_{0.9}Yb_{0.1}Nd_{0.3}O_x$ | 100 | >5 | 650 | 81.0 |
| Catalyst #5 | $Sr_{1.0}La_{0.9}Yb_{0.1}Nd_{0.7}O_x$ | 100 | >5 | 650 | 80.7 |
| Catalyst #6 | $Sr_{1.0}La_{0.9}Yb_{0.3}Nd_{0.7}O_x$ | 100 | >5 | 650 | 81.1 |
| Catalyst #7 | $Sr_{1.0}La_{1.8}Yb_{0.1}Nd_{0.7}O_x$ | 100 | >5 | 625 | 80.9 |
| Comparative Catalyst #1 | $Sr_{1.0}La_{0.9}Yb_{0.3}Nd_{0.7}O_x$ | 300-5000 | <5 | 725 | 78.7 |
| Comparative Catalyst #2 | $Sr_{1.0}La_{0.9}Yb_{0.3}Tm_{0.2}O_x$ | 300-5000 | <5 | 700 | 78.4 |
| Comparative Catalyst #3 | $Sr_{1.0}La_{2.5}Yb_{0.1}Nd_{0.7}O_x$ | 300-1000 | <5 | 625 | 75.6 |
| Comparative Catalyst #4 | $Sr_{1.0}La_{3.0}Yb_{0.1}Nd_{0.7}O_x$ | 300-1000 | <5 | 600 | 77.2 |

Note*:
Loaded with 10 mg catalyst

Figure 3:
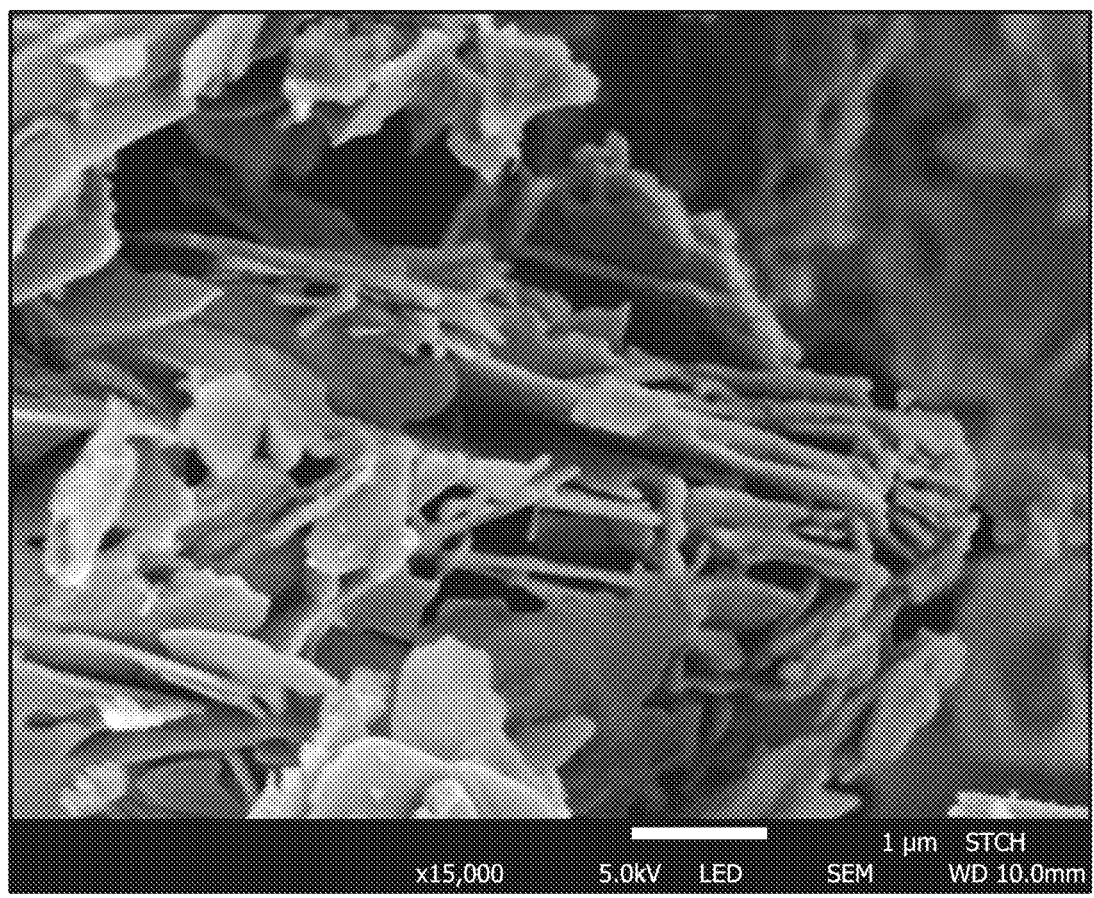
FIG. 3 displays a scanning electron microscope (SEM) micrograph of an OCM nanoplate catalyst composition.

The SEM image of catalyst #1 is shown in FIG. 3. It can be seen that the features of this catalyst have a structure of plate-like features (i.e., nanoplates), with the feature (i.e., nanoplate) thickness of 100 nm or less. With the thin nanoplates shown in FIG. 3, there will be less or no internal mass transfer resistance; such open and nanoplate features also provides the chance for more active sites be accessible to reactants, so that high activity can be obtained. Catalyst #1 has more than about 50 wt. % nanoplates, based on the total weight of the catalyst, wherein the amount of nanoplates was determined via the intercept method. Generally, the intercept method relies on drawing multiple lines across an SEM image. On each line, the numbers of all structural features, including plate-like features and nanoplate-like features, are counted, and thus the nanoplate content can be calculated as a % for any given line. By averaging the % nanoplate contents in all lines counted, the final % nanoplate content can be obtained for an SEM image of a given sample.

The best $C_{2+}$ selectivity obtained with this catalyst is 80.2%, which is also high compared to conventional OCM catalysts. The best selectivity obtained from different catalysts is used for comparison as shown in Table 1. The plate-like features (i.e., nanoplates) of the catalyst also bring about the open pore structure, which reduces the chance for the re-adsorption of methyl radicals and enhances the desorption of the products formed, therefore it will be beneficial to the product selectivity.

With high $O_2$ conversion and high $C_{2+}$ selectivity, high methane conversion (>20%) was obtained at 650° C. and beyond.

The plate features (i.e., nanoplates) are formed from rare earth (RE) hydroxides, which nanoplates can be described as two-dimensional corrugated plates, and are constituted by $RE^{3+}$-centered polyhedral units interconnected via hydroxyl groups and water vertexes. The counter anions, in this example, the $NO_3^-$, are accommodated in the hydroxide galleries by electrostatic interaction.

After thermal treatment, for example, calcination, the counter anions are removed from the material, resulting in a mixed oxide with plate-like features (i.e., nanoplates) as shown in FIG. 3. With specific conditions used, the material has a nanoplate thickness around 100 nm or less.

The schematic diagram of the plate-like feature (i.e., nanoplate) is shown in FIG. 1. t is the thickness of the nanoplate. From FIG. 3, we can see that t is about 100 nm or less for catalyst #1. Other two dimensions (l or w) are much larger than t. From FIG. 3, we can see that l or w are at least 10 times larger than t.

Catalyst #1 was also tested with 10 mg catalyst loading and with the same flow conditions as 20 mg loading, performance obtained is shown in Table 1. It can be seen that 700° C. is needed to get 90% $O_2$ conversion for 10 mg loading. Higher temperature is needed because of the lower catalyst loading used. The selectivity obtained under this condition is 80.3%.

Example 3

The performance and properties of catalysts #2, #3, #4, and #5 were investigated.

Figure 4:
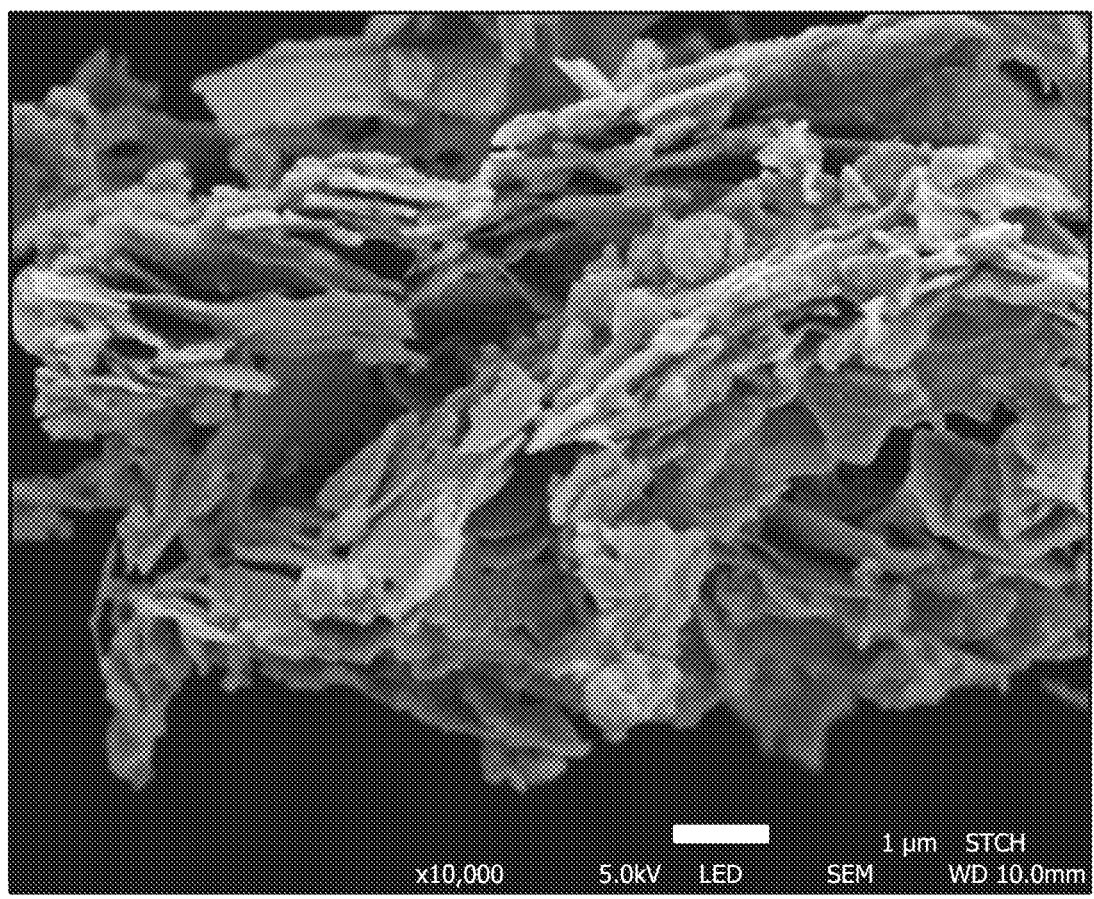
FIG. 4 displays a SEM micrograph of another OCM nanoplate catalyst composition.

Catalyst #2 ($Sr_{1.0}La_{1.8}Yb_{0.1}O_x$). Catalyst #2 has higher La content than catalyst #1. The performance of catalyst #2 is shown in Table 1 with 10 mg catalyst loading. More than 90% oxygen conversion was achieved at 650° C., indicating a higher activity than catalyst #1. The SEM of catalyst #2 is shown in FIG. 4. It can be seen that features of this catalyst also have the plate-like features (i.e., nanoplates). The thickness (t) of these plate-like features (i.e., nanoplates) are ~100 nm or less. l or w are at least 10 times larger than t. Catalyst #2 has more than about 50 wt. % nanoplates, based on the total weight of the catalyst, wherein the amount of nanoplates was determined by via the intercept method.

The best $C_{2+}$ selectivity obtained with this catalyst is 80.2%.

Catalyst #3 ($Sr_{1.0}La_{0.9}Nd_{0.1}Yb_{0.1}O_x$). Catalyst #3 has lower La content, but with Nd introduced into the catalyst. It was also prepared with the same method as catalyst #1.

The performance of catalyst #3 is shown Table 1. It can be seen that this catalyst reaches 90% or higher oxygen conversion at 650° C., indicating very high activity. The best $C_{2+}$ selectivity obtained with this catalyst is 80.2%.

Based on the SEM image of catalyst #3, this catalyst consists of plate-like features (i.e., nanoplates). The thickness (t) of these plate-like features (i.e., nanoplates) are ~100 nm or less. Other dimensions, l or w, are larger than t, with l or w>=5 t. The plate-like features (i.e., nanoplates) information is also shown in Table 1 for comparison. Catalyst #3 has more than about 50 wt. % nanoplates, based on the total weight of the catalyst, wherein the amount of nanoplates was determined via the intercept method.

Catalyst #4 ($Sr_{1.0}La_{0.9}Yb_{0.1}Nd_{0.3}O_x$). Catalyst #4 has higher Nd content compared to catalyst #3. It is also prepared using nitrates methods as catalyst #1. The performance of catalyst #2 is shown in Table 1. More than 90% oxygen conversion was achieved at 650° C., indicating a very high activity catalyst. The best $C_{2+}$ selectivity obtained with this catalyst is 81.0%.

Based on SEM image of catalyst #4, features of this catalyst have a structure of plate-like features (i.e., nanoplates). The thickness (t) of these plate-like features (i.e., nanoplates) are ~100 nm or less, and l or w was at least 5 times of t. Catalyst #4 has more than about 50 wt. % nanoplates, based on the total weight of the catalyst, wherein the amount of nanoplates was determined via the intercept method.

Catalyst #5 ($Sr_{1.0}La_{0.9}Yb_{0.1}Nd_{0.7}O_x$). Catalyst #5 has higher Nd content compared to catalyst #3. It is also prepared using nitrates methods as catalyst #1. The performance of catalyst #5 is shown in Table 1. More than 90% oxygen conversion was achieved at 650° C., indicating a very high activity catalyst. The best $C_{2+}$ selectivity obtained with this catalyst is 80.7%.

Based on SEM image of catalyst #5, features of this catalyst have a structure of plate-like features (i.e., nanoplates). The thickness (t) of these plate-like features (i.e., nanoplates) are ~100 nm or less, and l or w is at least 5 times of t. Catalyst #5 has more than about 50 wt. % nanoplates, based on the total weight of the catalyst, wherein the amount of nanoplates was determined via the intercept method.

Example 4

Catalyst #6 ($Sr_{1.0}La_{0.9}Yb_{0.3}Nd_{0.7}O_x$). Catalyst #6 has higher Yb content compared to catalyst #5. It is also prepared using nitrates methods as catalyst #1.

Figure 5:
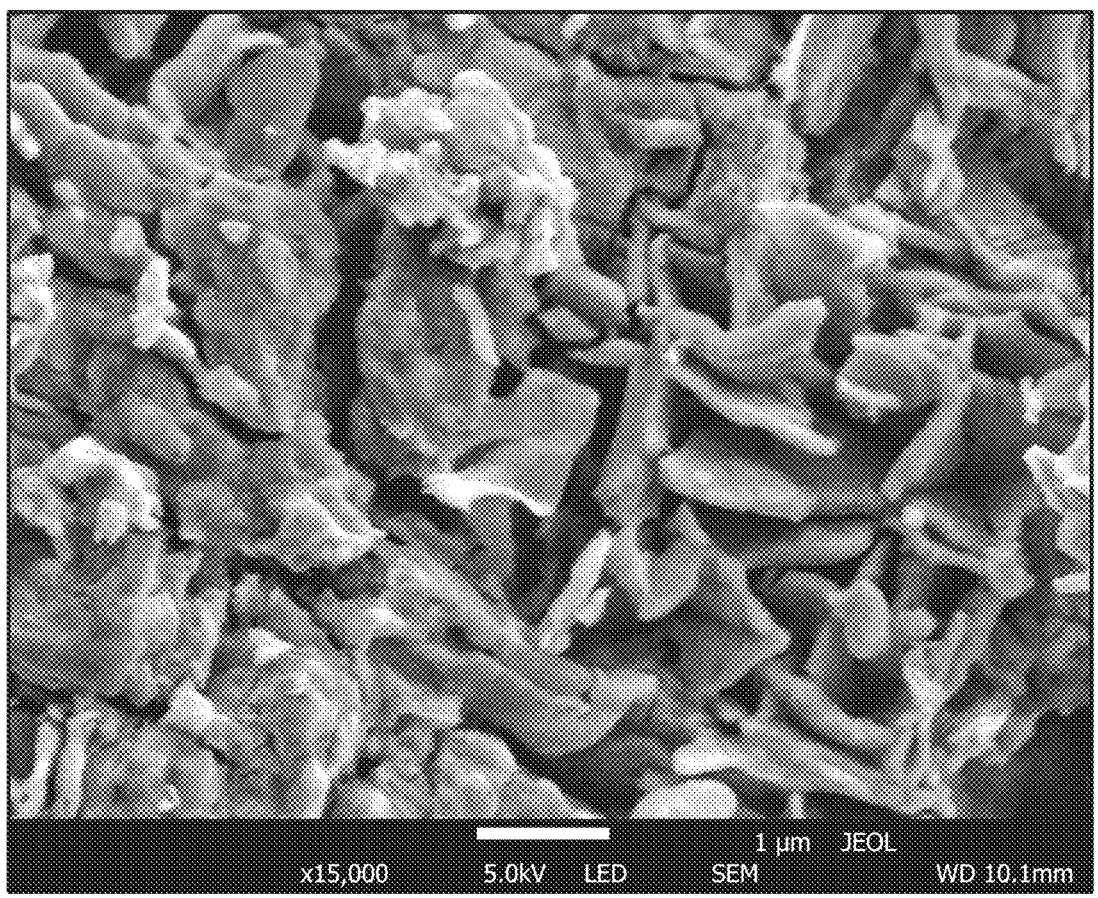
FIG. 5 displays a SEM micrograph of yet another OCM nanoplate catalyst composition.

Based on SEM image of catalyst #6, as shown in FIG. 5, features of this catalyst have a structure of plate-like features (i.e., nanoplates). The thickness (t) of these plate-like features (i.e., nanoplates) are ~100 nm or less, and l or w is at least 5 times of t. Catalyst #6 has more than about 50 wt. % nanoplates, based on the total weight of the catalyst, wherein the amount of nanoplates was determined via the intercept method.

Comparative Catalyst #1 ($Sr_{1.0}La_{0.9}Yb_{0.3}Nd_{0.7}O_x$). Comparative catalyst #1 has the same composition as catalyst #6, but was prepared differently. Comparative catalyst #1 was not prepared by the rare earth nitrates raw materials of as shown above, but by using rare earth oxides raw materials. 2.96 g of $SrCO_3$ nanoparticles, 2.94 g of $La_2O_3$ nanoparticles, 2.36 g of $Nd_2O_3$ nanoparticles and 1.19 g of $Yb_2O_3$ nanoparticles were used to prepare comparative catalyst #1. These rare earth oxides raw material solids were mixed with 40 ml D.I. water and the resulting mixture was dried at 120° C. for overnight and followed by calcination at 900° C. for 6 hours.

Figure 6:
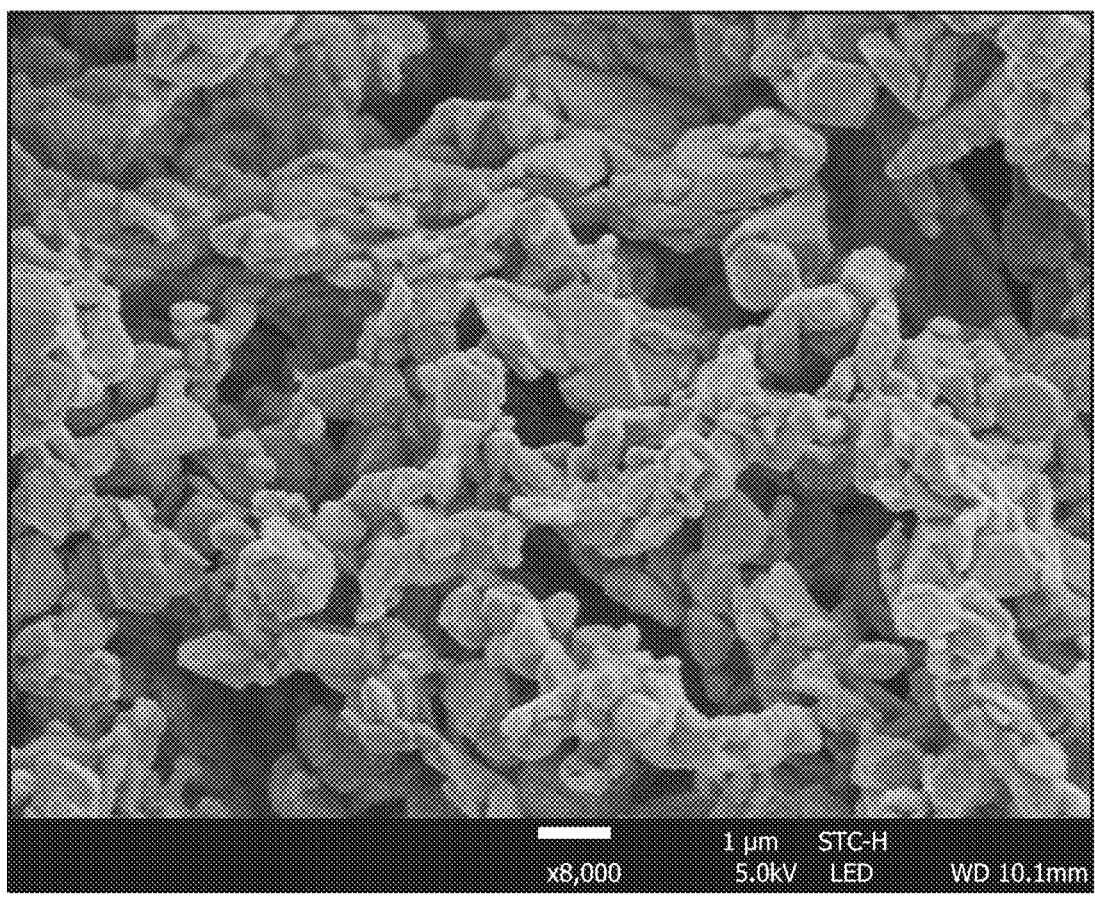
FIG. 6 displays a SEM micrograph of a comparative (reference) OCM catalyst.

The SEM image of comparative catalyst #1 is shown in FIG. 6. It can be seen that the structural features of this catalyst are clearly different from other catalysts, no plate-like features are observable in this catalyst (i.e., about 0 wt. % nanoplates, based on the total weight of the catalyst), wherein the amount of nanoplates was determined via the intercept method. The three dimensions of the observable structural features are all 300 nm or bigger, which is clearly different from the dimensions of catalyst #6.

Figure 7:
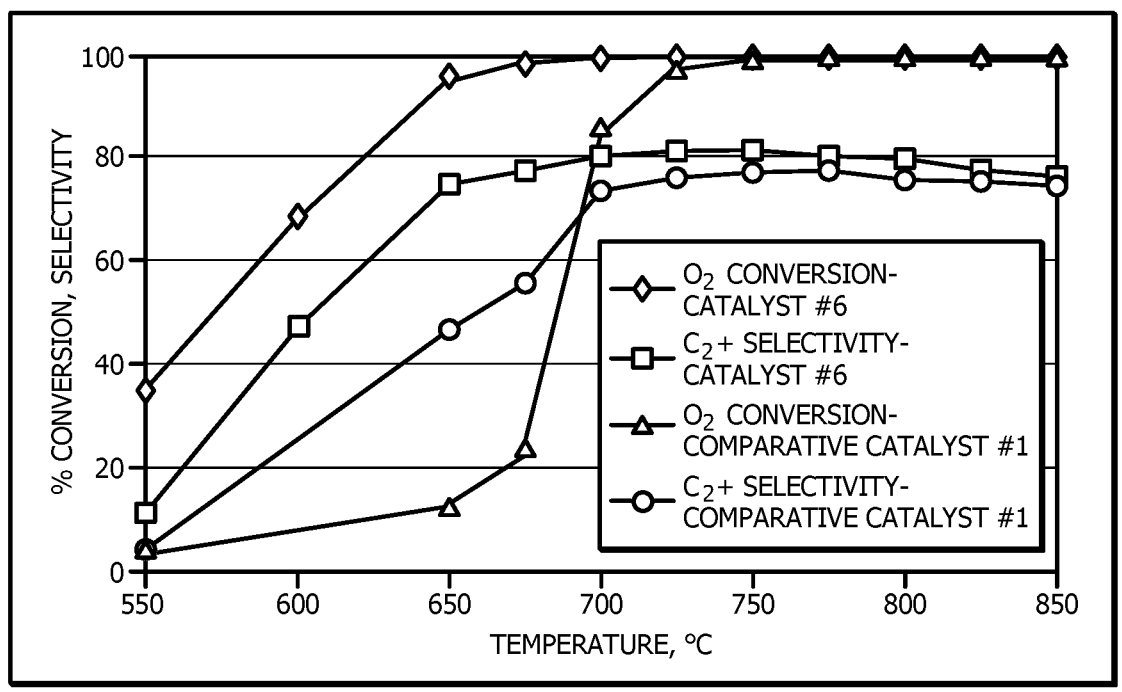
FIG. 7 displays a comparison graph of $C_{2+}$ selectivity and oxygen conversion as a function of temperature for an OCM nanoplate catalyst composition and a comparative (reference) OCM catalyst.
Figure 8:
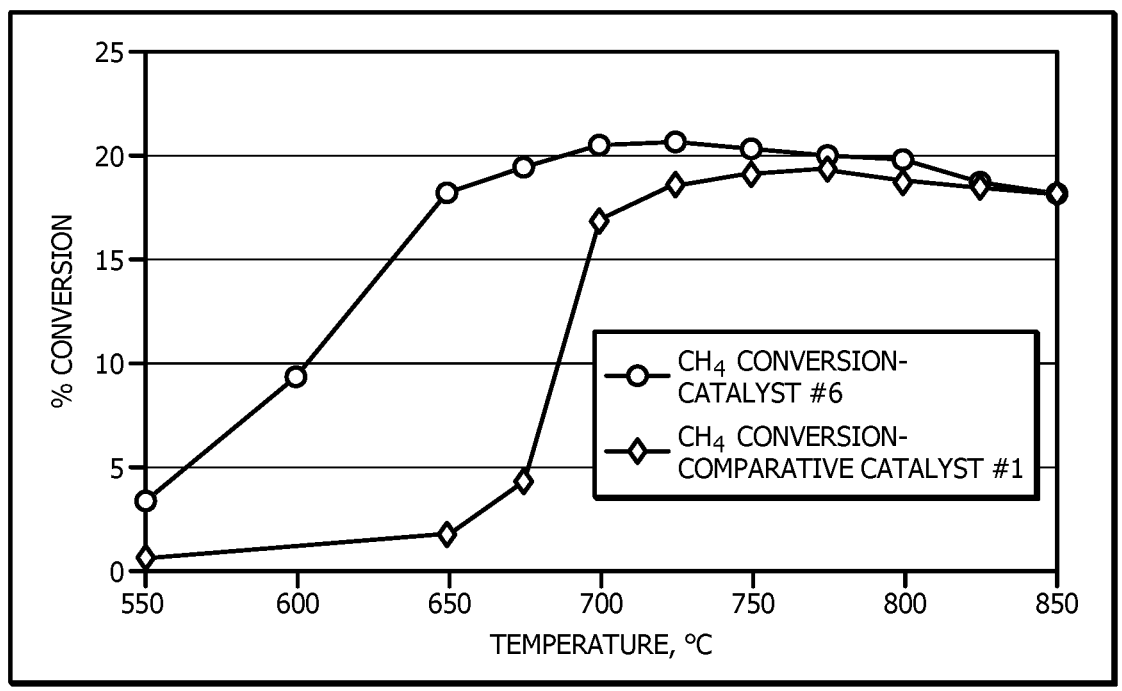
FIG. 8 displays a comparison graph of methane conversion as a function of temperature for an OCM nanoplate catalyst composition and a comparative (reference) OCM catalyst.

A comparison of catalytic performances of catalyst #6 and comparative catalyst #1 is shown in FIG. 7. The temperature to reach 90% $O_2$ conversion for catalyst #6 is 650° C., and the temperature to reach 90% $O_2$ conversion for comparative catalyst #1 is 725° C., indicating that catalyst #6 is clearly more active than comparative catalyst #1. The $C_{2+}$ selectivity of catalyst #6 is also clearly higher than that of comparative catalyst #1, as shown in FIG. 7. With higher $C_{2+}$ selectivity, the $CH_4$ conversion obtained with catalyst #6 is also higher than that of comparative catalyst #1, as shown in FIG. 8. With high $C_{2+}$ selectivity and higher $CH_4$ conversion, there will be higher productivity with catalyst #6 than with comparative catalyst #1.

The performance advantage of catalyst #6 comes from the nanoplate-like structure compared to comparative catalyst #1. Due to their differences in observable structural features, their surface area and pore structure are also different, as shown in Table 2.

With the plate-like structure, there will have higher surface area and more catalytic sites be accessible to reactants, as a result, high catalyst activity is obtained and a lower reaction temperature is needed to get the same conversion.

With the plate-like structure, it opens up the pore structure so that a higher pore volume is obtained. With the higher pore volume, the methyl radicals and products formed are easier to diffuse out without re-adsorption, as a result, higher selectivity is obtained.

TABLE 2

Surface area and pore volume comparison of catalyst #6 and comparative catalyst #1

|  | Surface Area (SA) ($m^2/g$) | Pore Volume (PV) (cc/g) |
| --- | --- | --- |
| Catalyst #6 | 2.5 | 0.033 |
| Comparative catalyst #1 | 1.0 | 0.012 |

Example 5

Catalyst #7 ($Sr_{1.0}La_{1.8}Yb_{0.1}Nd_{0.7}O_x$). Catalyst #7 has higher La content compared to catalyst #5. It is also prepared using nitrates methods as catalyst #1. The performance of catalyst #7 is shown in Table 1. More than 90% oxygen conversion was achieved at 625° C., indicating a very high activity catalyst. The best $C_{2+}$ selectivity obtained with this catalyst is 80.9%.

Based on SEM image of catalyst #7, features of this catalyst have a structure of plate-like features (i.e., nanoplates). The thickness (t) of these plate-like features (i.e., nanoplates) are ~100 nm or less, and l or w was at least 5 times of t. Catalyst #7 has more than about 50 wt. % nanoplates, based on the total weight of the catalyst, wherein the amount of nanoplates was determined via the intercept method.

Example 6

The performance and properties of comparative catalysts #2, #3, and #4 were investigated.

Comparative catalyst #2 ($Sr_{1.0}La_{0.9}Yb_{0.3}Tm_{0.2}O_x$). Compared to catalyst #3, comparative catalyst #1 has no Nd and has higher content of Yb and Tm. Comparative catalyst #1 was prepared by using nitrates.

The performance of comparative catalyst #2 is shown Table 1. It can be seen that this catalyst reaches 90% or higher oxygen conversion at 700° C., 50° C. higher than catalyst #3, indicating a lower catalyst activity. The $C_{2+}$ selectivity obtained with this catalyst is 78.4%, which is lower than catalyst #3.

Figure 9:
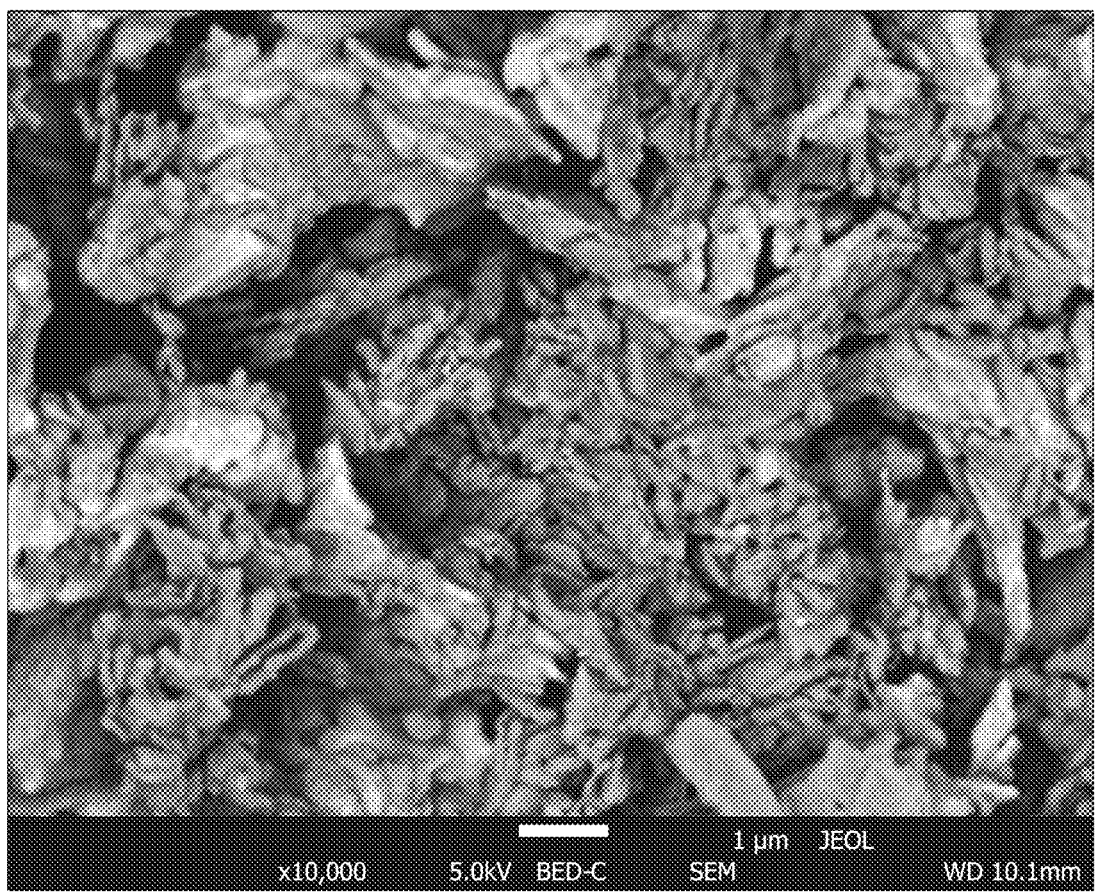
FIG. 9 displays a SEM micrograph of another comparative (reference) OCM catalyst.

The SEM image of comparative catalyst #2 is shown in FIG. 9. It can be seen that it does not have the plate-like features (i.e., nanoplates), different from the catalysts #1, #2, #3, #4, #5, #6 and #7 above. Regarding the three dimensions of the observable structural features, l, w and t are close to each other, and they are in the range of 300 to 5,000 nm. The thin plate (t) of 100 nm (i.e., nanoplate) could not be seen from this catalyst. The feature of other dimensions, l or w>5 t, was also not seen for comparative catalyst #1. Comparative catalyst #2 has no nanoplates (about 0 wt. % nanoplates, based on the total weight of the catalyst), wherein the amount of nanoplates was determined via the intercept method.

Comparative catalyst #3 ($Sr_{1.0}La_{2.5}Yb_{0.1}Nd_{0.7}O_x$). Compared to catalyst #7, comparative catalyst #3 has higher La content. Comparative catalyst #3 was prepared by using nitrates.

The performance of comparative catalyst #3 is shown Table 1. It can be seen that this catalyst reaches 90% or higher oxygen conversion at 625° C., indicating a higher catalyst activity, which is due to the higher La content. But, the $C_{2+}$ selectivity obtained with this catalyst is 75.6%, which is significantly lower than catalyst #7.

Figure 10:
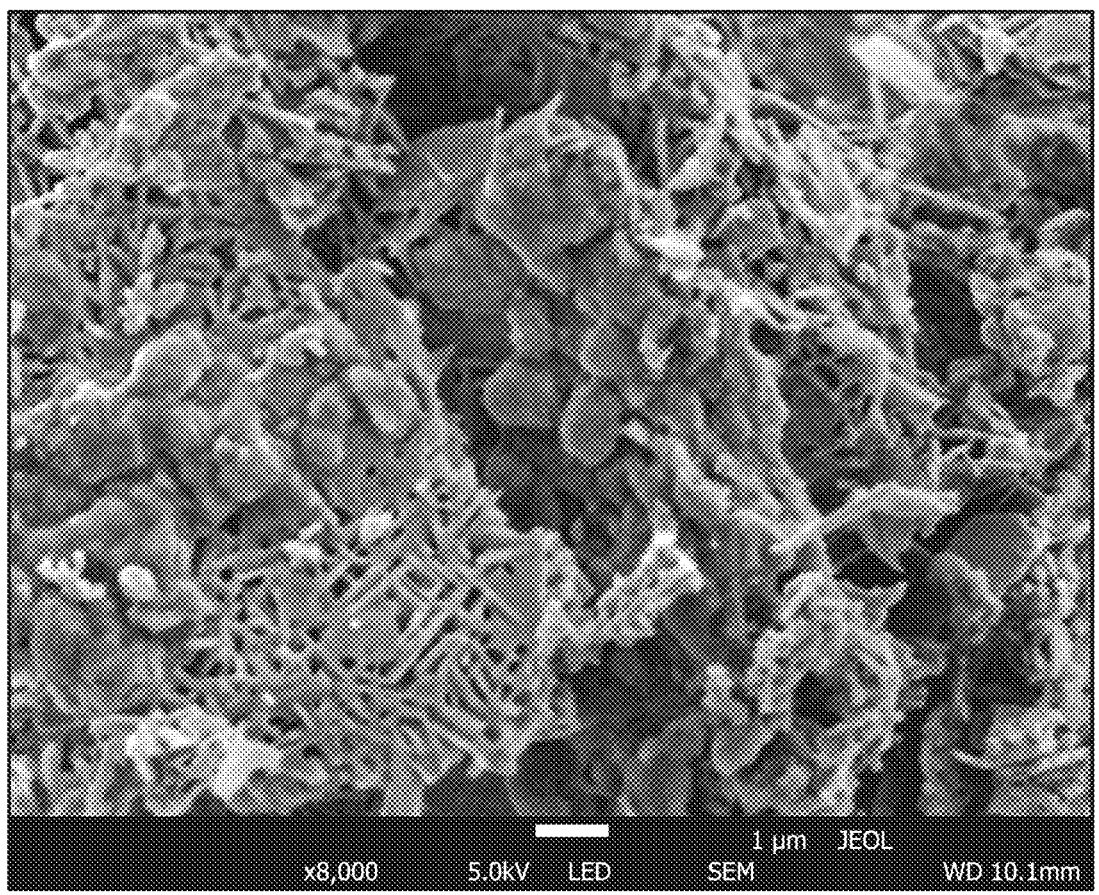
FIG. 10 displays a SEM micrograph of yet another comparative (reference) OCM catalyst.

The SEM image of comparative catalyst #3 is shown in FIG. 10. It can be seen that it have much less plate-like features, structural features of larger round geometry also exist in this catalyst. For most of the catalyst, the feature size, l, w and t are close to each other, and they are in the range of 300 to 1,000 nm. Thin features (t) of 100 nm are much less in this catalyst, so that the feature of other dimensions, l or w>5 t, was also not seen for comparative catalyst #3. Comparative catalyst #3 has less than about 25 wt. % nanoplates, based on the total weight of the catalyst, wherein the amount of nanoplates was determined via the intercept method.

Comparative catalyst #4 ($Sr_{1.0}La_{3.0}Yb_{0.1}Nd_{0.7}O_x$). Compared to catalyst #7, comparative catalyst #4 has even higher La content. Comparative catalyst #4 was prepared by using nitrates.

The performance of comparative catalyst #4 is shown Table 1. It can be seen that this catalyst reaches 90% or higher oxygen conversion at 600° C., indicating a higher catalyst activity which is due to the higher La content. But, the $C_{2+}$ selectivity obtained with this catalyst is 77.2%, which is lower than catalyst #7.

The SEM image of comparative catalyst #4 is similar to comparative catalyst #3; and comparative catalyst #4 also have much less plate-like features (less than about 25 wt. % nanoplates, based on the total weight of the catalyst), with larger round features also found in comparative catalyst #4. For most of the catalyst, the feature size, l, w and t are close to each other, and they are in the range of 300 to 1,000 nm. Thin features (t) of 100 nm are much less in this catalyst, so that the feature of other dimensions, l or w>5 t, was also not seen for comparative catalyst #4. Comparative catalyst #4 has less than about 25 wt. % nanoplates, based on the total weight of the catalyst, wherein the amount of nanoplates was determined via the intercept method.

It can be summarized from the above results that the nanoplate feature is critical for a catalyst to get a high activity and high selectivity. Such preferred nanoplate features are obtained when the catalyst compositions are in a very special range, that is, 1.0<=La+Nd<=3.0. When the La+Nd is less than 1.0, low activity and low selectivity catalyst is obtained. When the La+Nd is higher than 3.0, low selectivity is obtained.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

The invention claimed is:

1. An oxidative coupling of methane (OCM) nanoplate catalyst composition, comprising:
equal to or greater than about 25 wt. % nanoplates, based on the total weight of the OCM nanoplate catalyst composition; wherein a nanoplate is a three-dimensional object defined in accordance with ISO/TS 80004-2:2015; wherein a nanoplate is characterized by a first external dimension, a second external dimension, and a third external dimension; wherein the first external dimension is the thickness (t) of the nanoplate, and wherein t is equal to or less than about 100 nm; wherein the second external dimension is the length (l) of the nanoplate, and wherein l is greater than t; wherein the third external dimension is the width (w) of the nanoplate, and wherein w is greater than t; wherein l and w can be the same or different; and wherein (i) l>5t, (ii) w>5t, or (iii) l>5t and w>5t; and
wherein the OCM nanoplate catalyst composition is characterized by the general formula $A_aZ_bE_cD_dO_x$; wherein A is one or more alkaline earth metals; wherein Z is one or more first rare earth elements; wherein E is one or more second rare earth elements; wherein D is one or more redox agents or one or more third rare earth elements; wherein the one or more first rare earth elements, the one or more second rare earth elements, and the one or more third rare earth elements, when present, are not the same; wherein a is 1.0; wherein b is from about 1.0 to about 3.0; wherein c is from about 0 to about 1.5; wherein d is from about 0 to about 1.5; wherein b is greater than the sum of c and d (b>(c+d)); and wherein x balances the oxidation states.

2. The OCM nanoplate catalyst composition of claim 1, wherein the OCM nanoplate catalyst composition is characterized by an open pore structure.

3. The OCM nanoplate catalyst composition of claim 1, wherein the OCM nanoplate catalyst composition is characterized by a specific surface area that is increased by equal to or greater than about 20% when compared to a specific surface area of an otherwise similar OCM catalyst composition comprising less than about 25 wt. % nanoplates, based on the total weight of the composition.

4. The OCM nanoplate catalyst composition of claim 1, wherein the OCM nanoplate catalyst composition is characterized by a total pore volume that is increased by equal to or greater than about 10% when compared to a total pore volume of an otherwise similar OCM catalyst composition comprising less than about 25 wt. % nanoplates, based on the total weight of the composition.

5. The OCM nanoplate catalyst composition of claim 1, wherein the one or more alkaline earth metals is selected from the group consisting of magnesium (Mg), calcium (Ca), strontium (Sr), barium (Ba), and combinations thereof.

6. The OCM nanoplate catalyst composition of claim 1, wherein the one or more first rare earth elements is selected from the group consisting of lanthanum (La), neodymium (Nd), and combinations thereof.

7. The OCM nanoplate catalyst composition of claim 1, wherein the one or more second rare earth elements and the one or more third rare earth elements can each independently be selected from the group consisting of scandium (Sc), cerium (Ce), praseodymium (Pr), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

8. The OCM nanoplate catalyst composition of claim 1, wherein the one or more redox agents is selected from the group consisting of manganese (Mn), tungsten (W), bismuth (Bi), antimony (Sb), tin (Sn), cerium (Ce), praseodymium (Pr), and combinations thereof.

9. The OCM nanoplate catalyst composition of claim 1 comprising one or more oxides of A; one or more oxides of Z; one or more oxides of E; one or more oxides of D; or combinations thereof.

10. The OCM nanoplate catalyst composition of claim 1 having the general formula $A_aLa_bE_cO_x$; wherein E is one or more second rare earth elements; wherein a is 1.0; wherein b is from about 1.0 to about 3.0; wherein c is from about 0.01 to about 1.5; wherein b is greater than c; and wherein x balances the oxidation states.

11. The OCM nanoplate catalyst composition of claim 10, wherein d is 0; wherein the OCM nanoplate catalyst composition is characterized by the general formula $Sr_aLa_bYb_cO_x$; wherein a is 1.0; wherein b is from about 1.0 to about 3.0; wherein c is from about 0.01 to about 1.5; wherein b is greater than c; and wherein x balances the oxidation states.

12. The OCM nanoplate catalyst composition of claim 1 having the general formula $Sr_aLa_{b1}Nd_{b2}Yb_cO_x$; wherein a is 1.0; wherein b1 is from about 0.01 to about 2.99; wherein b2 is from about 0.01 to about 2.99; wherein b=(b1+b2); wherein b is from about 1.0 to about 3.0; wherein c is from about 0.01 to about 1.5; wherein b is greater than c; and wherein x balances the oxidation states.

13. The OCM nanoplate catalyst composition of claim 1 further comprising a support, wherein at least a portion of the OCM nanoplate catalyst composition contacts, coats, is embedded in, is supported by, and/or is distributed throughout at least a portion of the support; wherein the support comprises MgO, $Al_2O_3$, $SiO_2$, $ZrO_2$, $TiO_2$, or combinations thereof; and wherein the support is in the form of a powder, a particle, a pellet, a monolith, a foam, a honeycomb, or combinations thereof.

14. The OCM nanoplate catalyst composition of claim 1, wherein the one or more first rare earth elements is selected from the group consisting of lanthanum (La), neodymium (Nd), and combinations thereof; wherein D is one or more third rare earth elements; and wherein the one or more second rare earth elements and the one or more third rare earth elements can each independently be selected from the group consisting of scandium (Sc), cerium (Ce), praseodymium (Pr), promethium (Pm), samarium (Sm), europium (Eu), gadolinium (Gd), yttrium (Y), terbium (Tb), dysprosium (Dy), holmium (Ho), erbium (Er), thulium (Tm), ytterbium (Yb), lutetium (Lu), and combinations thereof.

15. The OCM nanoplate catalyst composition of claim 1, wherein b is from about 1.0 to about 2.5; wherein c is from about 0 to about 0.3; and wherein d is from about 0 to about 0.3.

16. A method of making an oxidative coupling of methane (OCM) nanoplate catalyst composition comprising:
(a) forming an OCM nanoplate catalyst precursor mixture; wherein the OCM nanoplate catalyst precursor mixture comprises a nitrate comprising one or more alkaline earth metal cations, a nitrate comprising one or more first rare earth element cations, a nitrate comprising one or more second rare earth element cations, and a nitrate comprising one or more redox agent cations or one or more third rare earth element cations; wherein the one or more first rare earth element cations, the one or more second rare earth element cations, and the one or more third rare earth element cations, when present, are not the same; wherein the OCM nanoplate catalyst precursor mixture is characterized by a molar ratio of one or more first rare earth elements to one or more alkaline earth metals of b:1, wherein b is from about 1.0 to about 3.0; wherein the OCM nanoplate catalyst precursor mixture is characterized by a molar ratio of one or more second rare earth elements to one or more alkaline earth metals of c:1, wherein c is from about 0 to about 1.5; wherein the OCM nanoplate catalyst precursor mixture is characterized by a molar ratio of one or more redox agents or one or more third rare earth elements to one or more alkaline earth metals of d:1, wherein d is from about 0 to about 1.5; and wherein b is greater than the sum of c and d (b>(c+d)); and (b) calcining at least a portion of the OCM nanoplate catalyst precursor mixture at a temperature of equal to or greater than about 750° C. to form the OCM nanoplate catalyst composition of claim 1.

17. The method of claim 16, wherein the step (a) of forming an OCM nanoplate catalyst precursor mixture further comprises (i) solubilizing the nitrate comprising one or more alkaline earth metal cations, the nitrate comprising one or more first rare earth element cations, the nitrate comprising one or more second rare earth element cations, and the nitrate comprising one or more redox agent cations or one or more third rare earth element cations in an aqueous medium to form an OCM nanoplate catalyst precursor aqueous solution; and (ii) drying at least a portion of the OCM nanoplate catalyst precursor aqueous solution at a temperature of equal to or greater than about 75° C. to form the OCM nanoplate catalyst precursor mixture.

18. The method of claim 17, wherein at least a portion of the OCM nanoplate catalyst precursor aqueous solution is contacted with a support to yield a supported OCM nanoplate catalyst precursor; and wherein at least a portion of the supported OCM nanoplate catalyst precursor is further dried and calcined to form the OCM nanoplate catalyst composition.

19. A method for producing olefins comprising:
(a) introducing a reactant mixture to an oxidative coupling of methane (OCM) reactor comprising the OCM nanoplate catalyst composition of claim 1, wherein the reactant mixture comprises methane ($CH_4$) and oxygen ($O_2$);
(b) allowing at least a portion of the reactant mixture to contact at least a portion of the OCM nanoplate catalyst composition and react via an OCM reaction to form a product mixture comprising unreacted methane and olefins;
(c) recovering at least a portion of the product mixture from the OCM reactor; and
(d) recovering at least a portion of the olefins from the product mixture.

20. The method of claim 19, wherein the OCM nanoplate catalyst composition is characterized by a $C_{2+}$ selectivity that is increased when compared to a $C_{2+}$ selectivity of an otherwise similar OCM catalyst composition comprising less than about 25 wt. % nanoplates, based on the total weight of the composition.

21. The method of claim 19, wherein the OCM nanoplate catalyst composition is characterized by an activity increase; wherein the activity increase is defined as a decrease in a reactor temperature effective for achieving an $O_2$ conversion of equal to or greater than about 90%; and wherein the reactor temperature effective for achieving an $O_2$ conversion of equal to or greater than about 90% of the OCM nanoplate catalyst composition is decreased by equal to or greater than about 25° C. when compared to a reactor temperature effective for achieving an $O_2$ conversion of equal to or greater than about 90% of an otherwise similar OCM catalyst composition comprising less than about 25 wt. % nanoplates, based on the total weight of the composition.

22. The method of claim 19, wherein the product mixture further comprises carbon dioxide ($CO_2$), and wherein the OCM nanoplate catalyst composition is characterized by a $CO_2$ selectivity that is decreased by equal to or greater than about 5% when compared to a $CO_2$ selectivity of an otherwise similar OCM catalyst composition comprising less than about 25 wt. % nanoplates, based on the total weight of the composition.

\* \* \* \* \*